(12) United States Patent
Takagi et al.

(10) Patent No.: US 9,445,783 B2
(45) Date of Patent: Sep. 20, 2016

(54) ULTRASOUND DIAGNOSTIC ADAPTER, ULTRASOUND DIAGNOSTIC APPARATUS, AND ULTRASOUND DIAGNOSTIC METHOD

(75) Inventors: Kazuya Takagi, Osaka (JP); Satoshi Kondo, Kyoto (JP)

(73) Assignee: KONICA MINOLTA, INC., Tokyo (JP)

( * ) Notice: Subject to any disclaimer, the term of this patent is extended or adjusted under 35 U.S.C. 154(b) by 958 days.

(21) Appl. No.: 13/479,785

(22) Filed: May 24, 2012

(65) Prior Publication Data

US 2012/0232401 A1 Sep. 13, 2012

Related U.S. Application Data

(63) Continuation of application No. PCT/JP2011/005312, filed on Sep. 21, 2011.

(30) Foreign Application Priority Data

Sep. 27, 2010 (JP) ................................ 2010-215376

(51) Int. Cl.
*A61B 8/00* (2006.01)
*A61B 8/08* (2006.01)

(52) U.S. Cl.
CPC ............. *A61B 8/4245* (2013.01); *A61B 8/429* (2013.01); *A61B 8/4209* (2013.01); *A61B 8/4272* (2013.01); *A61B 8/4444* (2013.01);
(Continued)

(58) Field of Classification Search
CPC . A61B 8/4461; A61B 8/4494; A61B 8/4245
See application file for complete search history.

(56) References Cited

U.S. PATENT DOCUMENTS 4,794,930 A   1/1989  Machida et al.
5,834,687 A * 11/1998 Talbot et al. ................. 174/386
7,112,173 B1 * 9/2006  Kantorovich et al. ........ 600/449
(Continued)

FOREIGN PATENT DOCUMENTS

JP    63-89147     4/1988
JP    04183453 A   6/1992
(Continued)

OTHER PUBLICATIONS

International Search Report issued Nov. 1, 2011 in International (PCT) Application No. PCT/JP2011/005312.
(Continued)

*Primary Examiner* — Rochelle Turchen
(74) *Attorney, Agent, or Firm* — Holtz, Holtz & Volek PC

(57) ABSTRACT

An ultrasound diagnostic adapter used when diagnosing a subject using an ultrasound probe that transmits and receives ultrasound waves, the ultrasound diagnostic adapter includes: a pad which has (i) a main surface that is a surface on a side where the ultrasound probe is disposed, and (ii) a back surface that is a surface which is opposite to the main surface and is on a side where the subject is disposed; and a first reflective member which is disposed inside the pad and made from a material having a different acoustic impedance than a material included in the pad, wherein the first reflective member is disposed such that at least one of (i) a distance between the first reflective member and the main surface and (ii) a width of the first reflective member viewed from the side of the main surface varies depending on a position in the main surface.

26 Claims, 27 Drawing Sheets

(52) U.S. Cl.
CPC .............. *A61B 8/463* (2013.01); *A61B 8/483* (2013.01); *A61B 8/4254* (2013.01)

(56) References Cited

U.S. PATENT DOCUMENTS

| | | | |
|---|---|---|---|
| 7,888,847 B2* | 2/2011 | Dietz et al. ............... | 310/334 |
| 2005/0288587 A1* | 12/2005 | Roh et al. ............... | 600/445 |
| 2007/0197914 A1* | 8/2007 | Kosaku ............... | 600/459 |
| 2011/0015524 A1* | 1/2011 | Suzuki et al. ............... | 600/443 |
| 2011/0040186 A1 | 2/2011 | Matsumura | |
| 2011/0040187 A1 | 2/2011 | Matsumura | |
| 2011/0306886 A1* | 12/2011 | Daft et al. ............... | 600/459 |

FOREIGN PATENT DOCUMENTS

| | | |
|---|---|---|
| JP | 07184899 A | 7/1995 |
| JP | 2001-157680 | 6/2001 |
| JP | 2002-102223 | 4/2002 |
| JP | 2003-334192 | 11/2003 |
| JP | 2006247203 A | 9/2006 |
| JP | 4137516 | 8/2008 |
| JP | 2008-200096 | 9/2008 |
| JP | 2009-268640 | 11/2009 |
| JP | 4611064 | 1/2011 |
| JP | 2012029718 A | 2/2012 |
| WO | 2009/131028 | 10/2009 |
| WO | 2009/131029 | 10/2009 |

OTHER PUBLICATIONS

Chinese Office Action dated Jul. 2, 2014 in counterpart Chinese Application No. 201180004643.8.

Japanese Office Action (and English translation thereof) dated Oct. 27, 2015, issued in counterpart Japanese Application No. 2012-502339.

* cited by examiner

| Number of pixels | Position of ultrasound probe [mm] |
|---|---|
| 5 | 0 |
| 6 | 5 |
| 7 | 10 |
| 8 | 15 |
| 9 | 20 |

•
•
•

| 22 | 85 |
|---|---|
| 23 | 90 |
| 24 | 95 |
| 25 | 100 |

FIG. 15
Scan direction of ultrasound probe
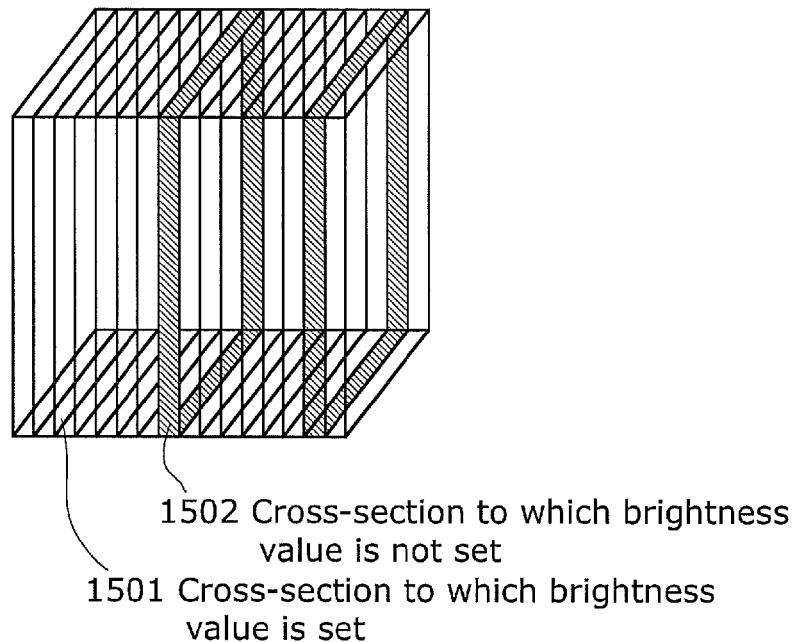
1502 Cross-section to which brightness value is not set
1501 Cross-section to which brightness value is set
FIG. 16
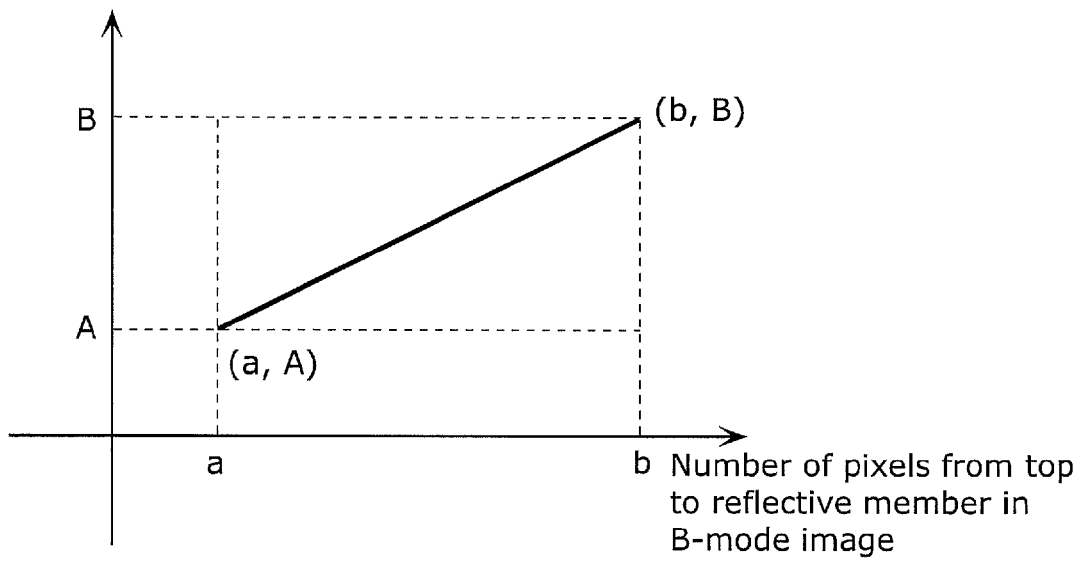

ULTRASOUND DIAGNOSTIC ADAPTER, ULTRASOUND DIAGNOSTIC APPARATUS, AND ULTRASOUND DIAGNOSTIC METHOD

CROSS REFERENCE TO RELATED APPLICATIONS

This is a continuation application of PCT Patent Application No. PCT/JP2011/005312 filed on Sep. 21, 2011, designating the United States of America, which is based on and claims priority of Japanese Patent Application No. 2010-215376 filed on Sep. 27, 2010. The entire disclosures of the above-identified applications, including the specifications, drawings and claims are incorporated herein by reference in their entirety.

TECHNICAL FIELD

Adapters, apparatuses and methods consistent with one or more exemplary embodiments of the present disclosure relate generally to ultrasound diagnostic adapters, ultrasound diagnostic apparatuses, and ultrasound diagnostic methods used when diagnosing subjects using ultrasound probes.

BACKGROUND ART

Ultrasound diagnostic apparatuses are diagnostic apparatuses that obtain information inside the body using ultrasound waves which reflect within living bodies, and display the information as ultrasound images. Ultrasound diagnostic apparatuses have been used as useful apparatuses which make it possible to observe conditions inside the body non-invasively.

According to the disclosure of Patent Literature 1, a correlation among a plurality of images obtained by scanning an ultrasound probe is calculated to obtain the distance between the images, and a three-dimensional image is produced by combining the images based on the distance between the images.

Furthermore, according to the disclosure of Patent Literature 2, an ultrasound probe moving mechanism including rails and a spiral spring is provided to move the ultrasound probe at a constant speed, and a three-dimensional image is produced by combining B-mode images taken at predetermined positions.

CITATION LIST

Patent Literature

[Patent Literature 1] Japanese Unexamined Patent Application Publication No. 2003-334192
[Patent Literature 2] Japanese Unexamined Patent Application Publication No. 2008-200096

SUMMARY OF INVENTION

Technical Problem

However, with the method disclosed in Patent Literature 1, it is not possible to detect that the ultrasound probe is physically moving, when similarity (continuity) in tissue distribution of a subject is high. Furthermore, errors accumulate as the distance traveled by the ultrasound probe increases.

Furthermore, Patent Literature 2 uses a moving mechanism to move the ultrasound probe at a constant speed, and thus compactness is compromised.

Solution to Problem

In view of the circumstances, one or more exemplary embodiments of the present disclosure may overcome the above disadvantages and other disadvantages not described herein. However, it is understood that one or more exemplary embodiments of the present disclosure are not required to overcome or may not overcome the disadvantages described above and other disadvantages not described herein. One or more exemplary embodiments of the present disclosure provide an ultrasound diagnostic adapter and the like with which a position of an ultrasound probe is detected without (i) depending on a scan rate of the ultrasound probe and a composition distribution (similarity) of a subject, (ii) accumulating errors, and (iii) compromising a compactness.

In order to provide the above-described ultrasound diagnostic adapter and the like, an ultrasound diagnostic adapter according to an exemplary embodiment of the present disclosure is an ultrasound diagnostic adapter to be interposed between an ultrasound probe and a subject and used when diagnosing the subject using the ultrasound probe, the ultrasound probe transmitting and receiving ultrasound waves, the ultrasound diagnostic adapter includes: a pad which has (i) a main surface that is a surface on a side where the ultrasound probe is disposed, and (ii) a back surface that is a surface which is opposite to the main surface and is on a side where the subject is disposed; and a first reflective member which is disposed inside the pad and made from a material having an acoustic impedance different from an acoustic impedance of a material included in the pad, wherein the first reflective member is disposed such that at least one of (i) a distance between the first reflective member and the main surface and (ii) a width of the first reflective member as seen from the side of the main surface varies depending on a position in the main surface.

It should be noted that these exemplary embodiments can be implemented either generally or specifically as a system, a method, an integrated circuit, a computer program, a recording medium, or any combination of a system, a method, an integrated circuit, a computer program, and a recording medium.

Advantageous Effects of Invention

According to various exemplary embodiments of the present disclosure, a function is added to a general ultrasound diagnostic apparatus. Thus, the position and an amount of movement of an ultrasound probe can be detected without (i) depending on a scan rate of the ultrasound probe and a composition distribution (similarity) of a subject, (ii) accumulating errors, and (iii) compromising compactness, and an ultrasound diagnose image such as a B-mode image and a three-dimensional image can be obtained.

BRIEF DESCRIPTION OF DRAWINGS

These and other advantages and features of exemplary embodiments of the present disclosure will become apparent from the following description thereof taken in conjunction with the accompanying Drawings that illustrate general and specific exemplary embodiments of the present disclosure. In the Drawings.

Figure 12:
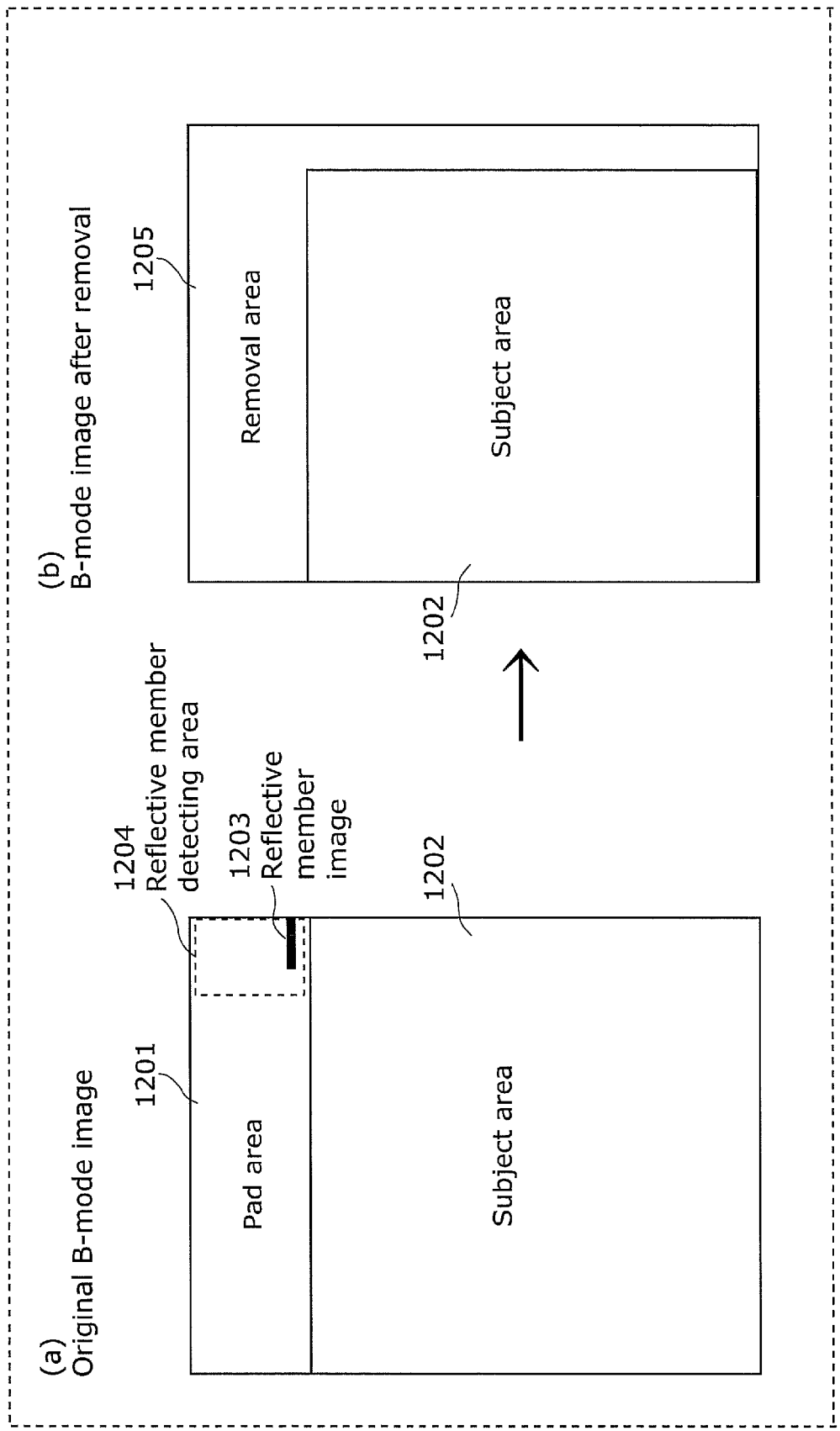
Figures 13, 14:
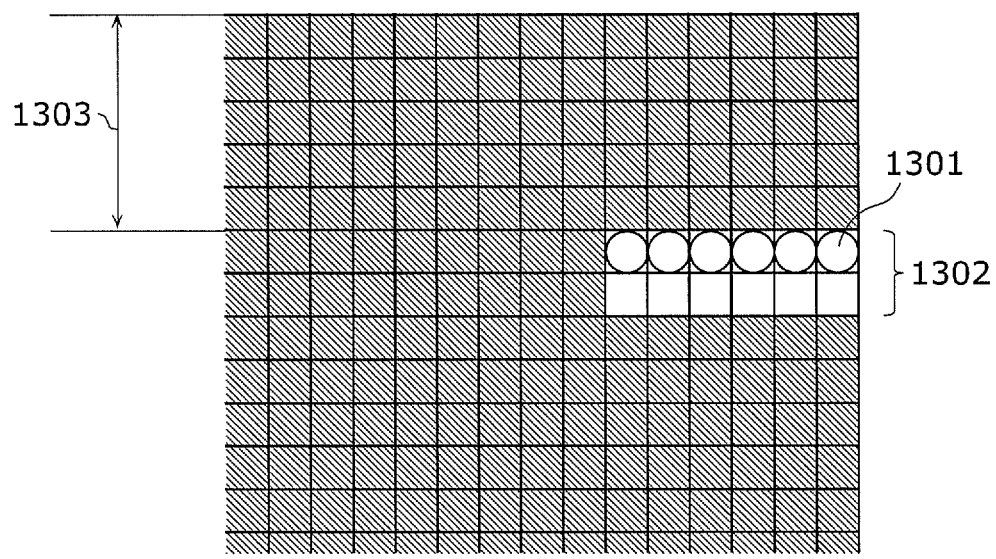
Figure 18:
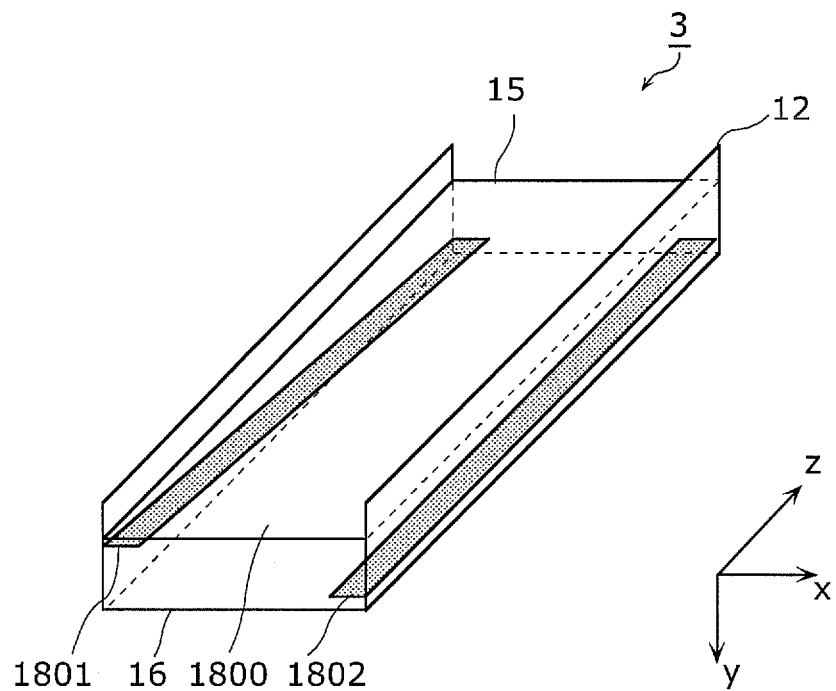
Figure 20:
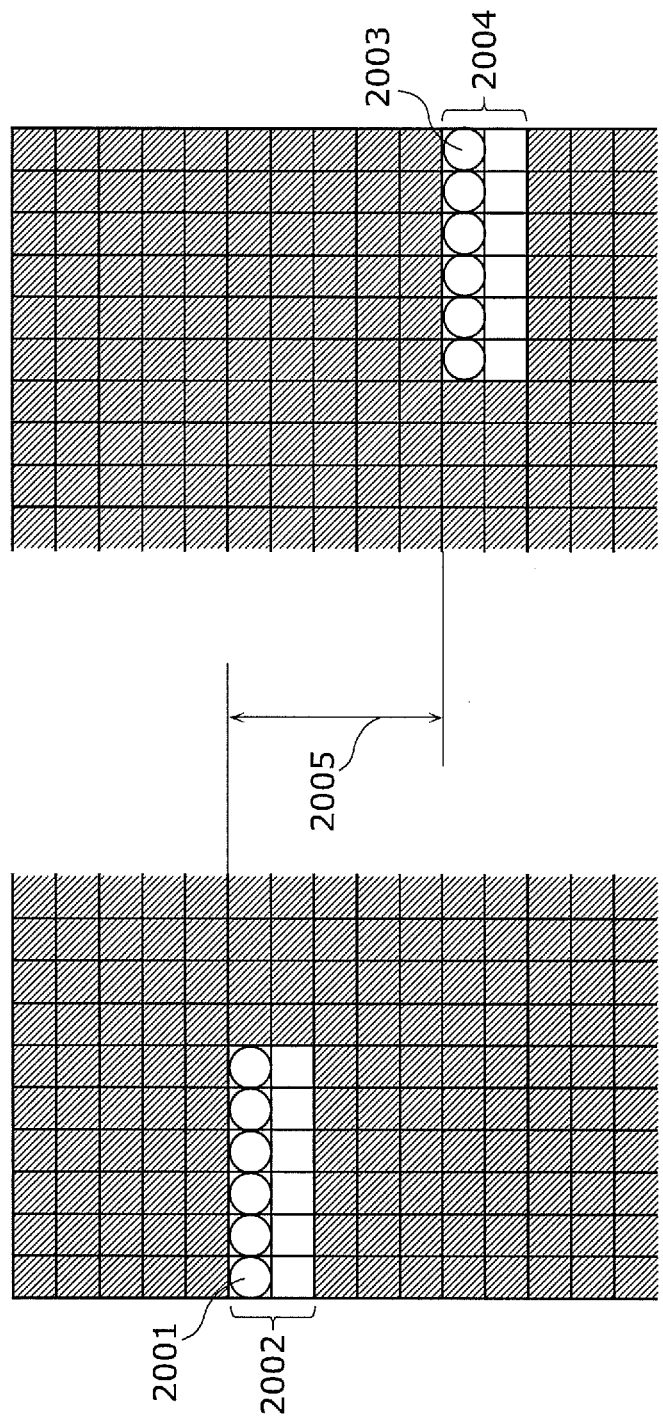
Figure 24:
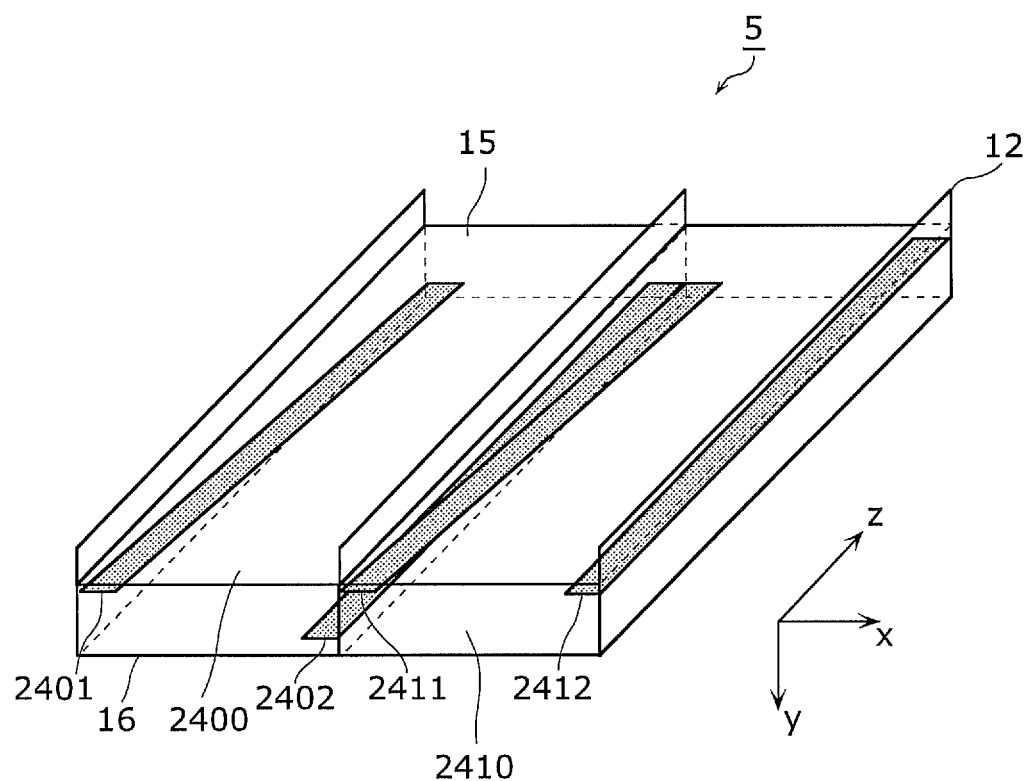
Figure 26:
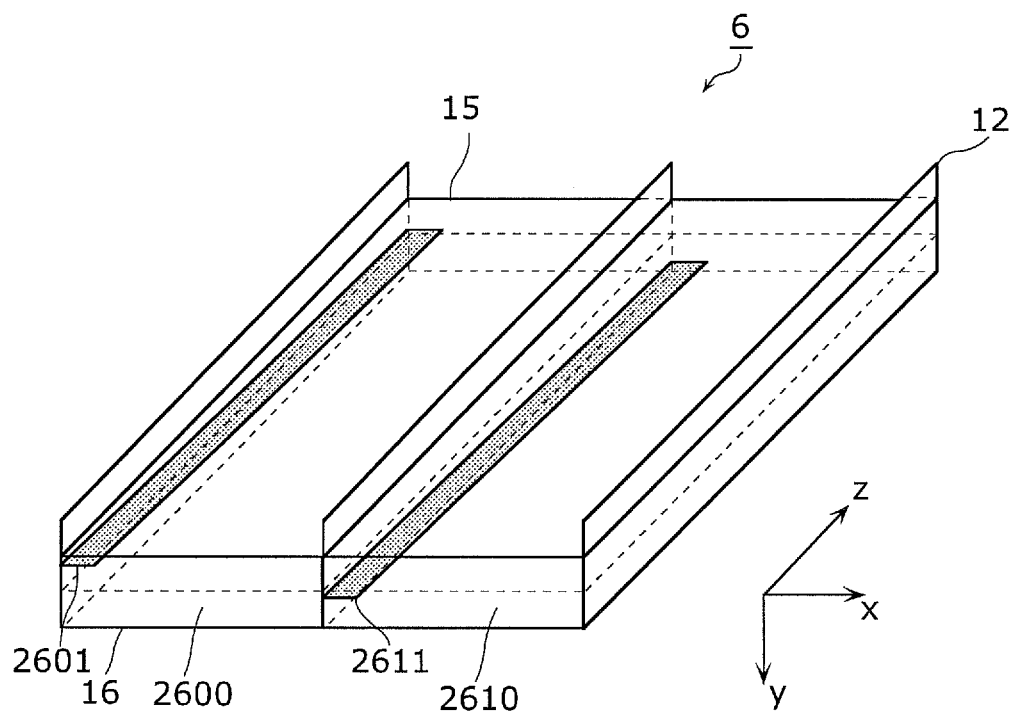
Figure 30:
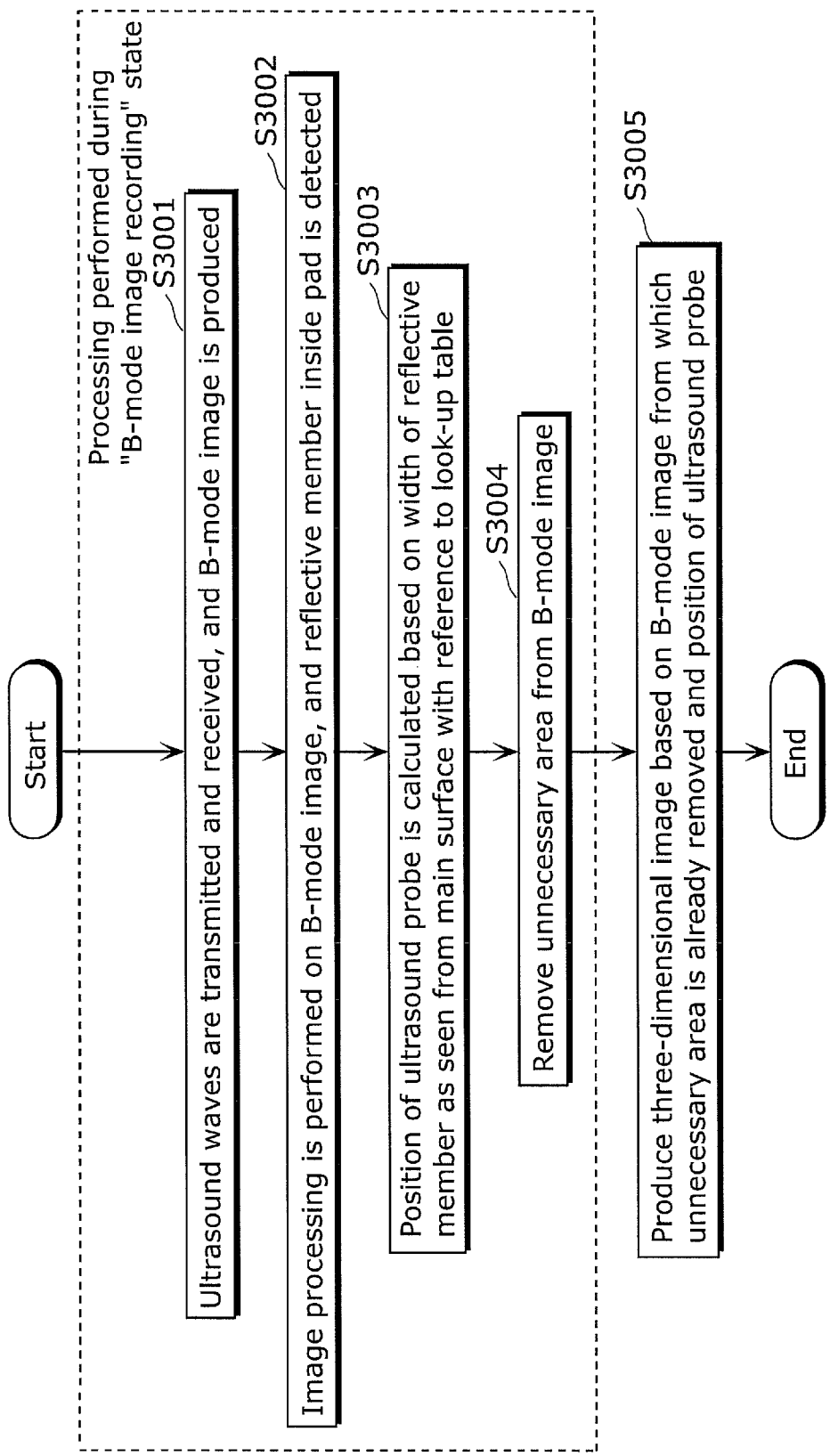
Figure 31:
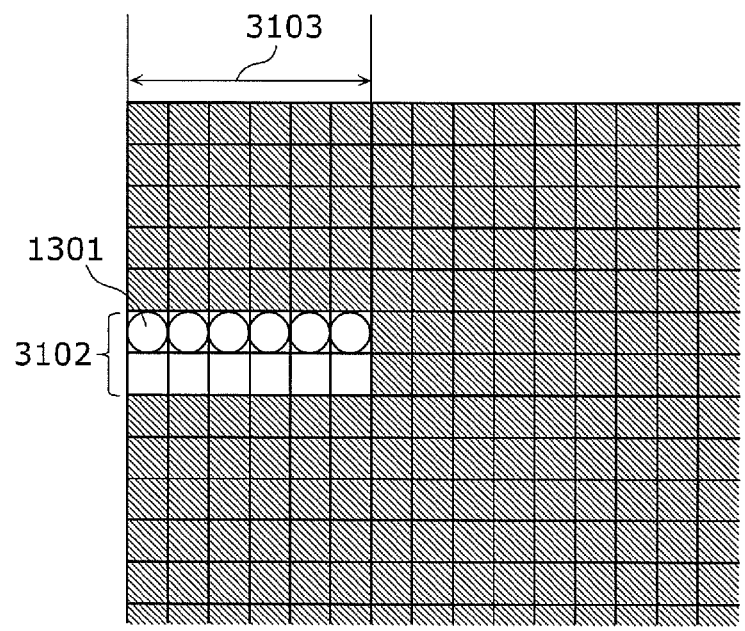
Figure 33:
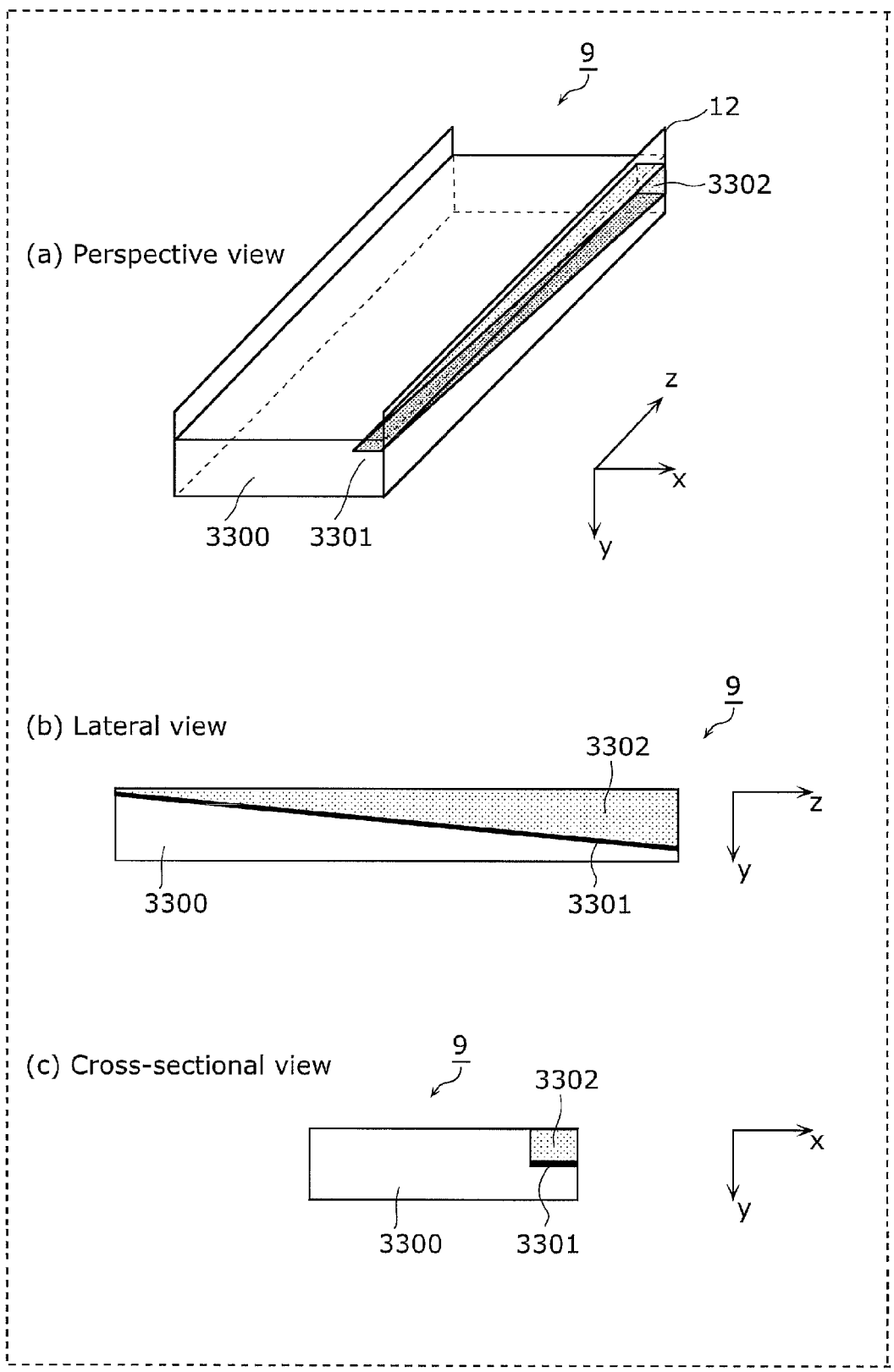
Figure 34:
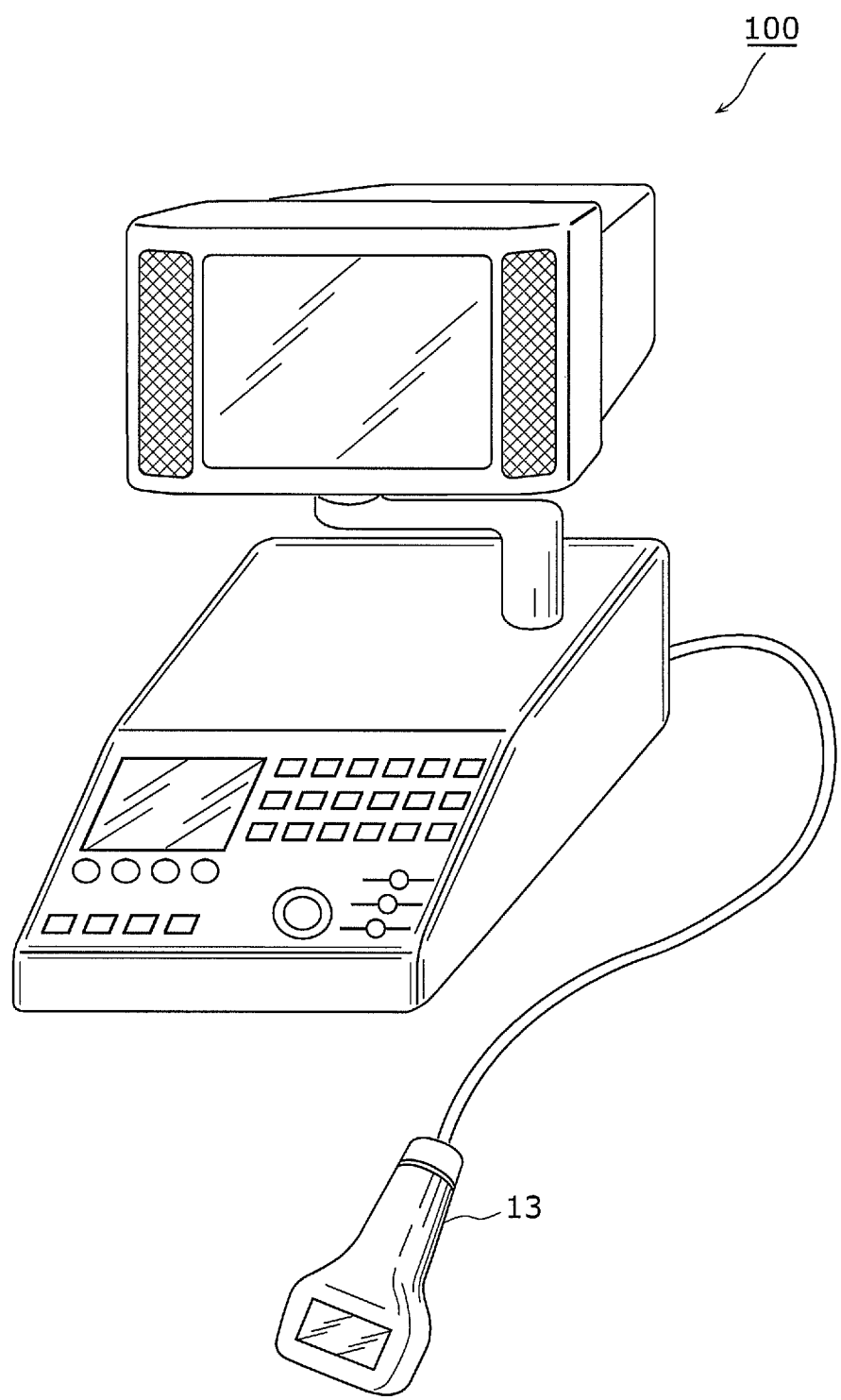

(a) in FIG. 12 is a diagram showing an obtained B-mode image, and (b) in FIG. 12 is a diagram for describing an unnecessary area to be removed from the B-mode image;

FIG. 13 is a diagram which describes a detection of a reflective member image in a B-mode image according to Embodiment 2;

FIG. 14 is a diagram showing an example of a look-up table;

FIG. 15 is a diagram for describing an interpolation for producing a three-dimensional image;

FIG. 16 is a diagram for describing a calibration method of the look-up table;

FIGS. 17(a) and (b) are diagrams for describing an issue of an ultrasound diagnostic adapter according to Embodiment 3;

FIG. 18 is a perspective view of a pad in which two reflective members according to Embodiment 3 are disposed;

FIGS. 19(a) and (b) are views showing lateral surfaces of the pad according to Embodiment 3;

FIG. 20 is a diagram showing positions of a reflective member in a B-mode image;

FIG. 21(a) is a diagram of an obtained B-mode image, and FIG. 21(b) is a diagram for describing an unnecessary area to be removed from the B-mode image;

FIGS. 22(a) and (b) are diagrams which describe an effect of solving the issue of Embodiment 3;

FIGS. 23(a), (b) and (c) are diagrams showing an ultrasound diagnostic adapter according to a variation of Embodiment 3;

FIG. 24 is a diagram showing an ultrasound diagnostic adapter according to Embodiment 4;

FIGS. 25(a), (b), (c) and (d) are lateral views of pads according to Embodiment 4;

FIG. 26 is a diagram showing pads according to Variation 1 of Embodiment 4;

FIGS. 27(a) and (b) are views showing lateral surfaces of the pads according to Variation 1 of Embodiment 4;

FIGS. 28(a) and (b) are a top view and a perspective view of an ultrasound diagnostic adapter according to Variation 3 of Embodiment 4, respectively;

FIGS. 29(a) and (b) are a top view and a perspective view of an ultrasound diagnostic adapter according to Embodiment 5, respectively;

FIG. 30 is a diagram which describes operations of a three-dimensional image displaying mechanism according to Embodiment 5;

FIG. 31 is a diagram showing a position of a reflective member in a B-mode image according to Embodiment 5;

FIGS. 32(a) and (b) are graphs which describe receipt time of reflected waves (echo) of ultrasound waves which propagate through substances having different acoustic velocities;

FIGS. 33(a), (b), and (c) are diagrams showing an ultrasound diagnostic adapter according to Embodiment 6; and FIG. 34 is an outline view of an ultrasound diagnostic apparatus.

DESCRIPTION OF EMBODIMENTS

Underlying Knowledge Forming Basis of the Present Disclosure

The inventors of the present disclosure found the following problems.

Ultrasound diagnostic apparatuses are diagnostic apparatuses that obtain information inside the body using ultrasound waves which reflect within living bodies, and display the information as ultrasound images. Ultrasound diagnostic apparatuses have been used as useful apparatuses which make it possible to observe conditions inside the body non-invasively.

An outline view of an ultrasound diagnostic apparatus is shown in FIG. 34. The ultrasound diagnostic apparatus transmits and receives ultrasound waves using an ultrasound probe 13. The ultrasound probe includes ultrasound transducers that transmit and receive ultrasound waves. The ultrasound probe causes ultrasound wave pulses, which are produced and transmitted by the ultrasound transducers, to incident on a subject, and receives reflected waves (echo) of ultrasound waves which reflected back. The ultrasound diagnostic apparatus displays characteristics of an echo from the subject as an image. Examples of image displaying systems include: a two-dimensional image displaying system which associates an amplitude of echo with brightness of a pixel so as to display a tomographic image of a subject (hereinafter referred to as a B-mode image); and a three-dimensional image displaying system which produces and displays a three-dimensional image by using a plurality of B-mode images.

The three-dimensional image displaying system allows an operator to easily comprehend the positional relationship of tissue, leading to an increased objectivity in diagnosis, and thus the three-dimensional image displaying system is very useful in a clinical setting. The three-dimensional image can be formed using, for example, a 3D oscillating probe and a position sensor.

When the oscillating probe is used to produce a three-dimensional image, the oscillating probe which oscillates an array elements that are elements of an ultrasound transducer arranged in one dimension is put on a surface of a body over a site of interest. Further, a four-dimensional (4D) function that reproduces three-dimensional images as a moving picture can be realized by rapidly oscillating the oscillating probe.

However, when information inside the body over a wide area is desired to be displayed as a three-dimensional image by using the oscillating probe, an oscillation mechanism becomes large, which leads to an increase in weight of the oscillation mechanism. Thus, there are problems, that is, operability of the ultrasound probe is impaired, and a subject feels chocked due to compression, especially when the neck and the like are diagnosed.

When a position sensor is used to produce a three-dimensional image, the position sensor is attached to a small, light-weight one-dimensional probe which includes transducers arranged in one dimension. As position sensors, a magnetic sensor and a sensor using an arm are already available. However, such sensors are expensive, which is a problem.

In view of the problems, according to the disclosure of Patent Literature 1, a correlation among a plurality of images obtained by scanning an ultrasound probe is calculated to obtain the distance between the images, and a three-dimensional image is produced by combining the images based on the distance between the images. This method is advantageous in that the position sensor is not used, and a high degree of freedom in scanning the ultrasound probe is ensured.

Furthermore, according to the disclosure of Patent Literature 2, an ultrasound probe moving mechanism including rails and a spiral spring is provided to move the ultrasound probe at a constant speed, and a three-dimensional image is produced by combining B-mode images taken at predetermined positions. This method is advantageous in that a B-mode image can be obtained precisely at a predetermined position, and the cost is relatively low.

However, the method disclosed in Patent Literature 1 has a problem in that it is not possible to detect that the ultrasound probe is physically moving, when similarity (continuity) in tissue distribution of a subject is high. This is because the distances between the images are determined based on the correlation among images. There is also a problem that errors accumulate as the distance traveled by the ultrasound probe increases.

Furthermore, Patent Literature 2 is described based on a premise that a scan rate of the ultrasound probe is kept at a constant speed with a spiral spring. Since a moving mechanism to allow the movement at a constant speed is used, compactness is compromised.

In view of the circumstances, one or more exemplary embodiments of the present disclosure provide an ultrasound diagnostic adapter and the like with which the position of an ultrasound probe is detected without (i) depending on a scan rate of the ultrasound probe and a composition distribution (similarity) of a subject, (ii) accumulating errors, and (iii) compromising a compactness.

In order to provide the above-described ultrasound diagnostic adapter and the like, an ultrasound diagnostic adapter according to an exemplary embodiment of the present disclosure is an ultrasound diagnostic adapter to be interposed between an ultrasound probe and a subject and used when diagnosing the subject using the ultrasound probe, the ultrasound probe transmitting and receiving ultrasound waves, the ultrasound diagnostic adapter includes: a pad which has (i) a main surface that is a surface on a side where the ultrasound probe is disposed, and (ii) a back surface that is a surface which is opposite to the main surface and is on a side where the subject is disposed; and a first reflective member which is disposed inside the pad and made from a material having an acoustic impedance different from an acoustic impedance of a material included in the pad, wherein the first reflective member is disposed such that at least one of (i) a distance between the first reflective member and the main surface and (ii) a width of the first reflective member as seen from the side of the main surface varies depending on a position in the main surface.

Thus, an image of the first reflective member is included in a B-mode image. At least one of the position and the shape of the first reflective member image in the B-mode image varies depending on a position of the ultrasound probe in the main surface. Thus, a position of the ultrasound probe in the main surface may be associated with a position and a shape of the first reflective member in the B-mode image beforehand. With this, a position of the ultrasound probe can be precisely detected based on the position and the shape of the first reflective member in the B-mode image obtained during the diagnosis.

For example, according to an exemplary embodiment of the present disclosure, the first reflective member extends inside the pad, and the ultrasound diagnostic adapter further comprises a second reflective member which extends inside the pad along an extending direction of the first reflective member and is made from a material having an acoustic impedance different from the acoustic impedance of the material included in the pad, wherein the first reflective member and the second reflective member are disposed such that an inclination angle of the first reflective member is different from an inclination angle of the second reflective member, the inclination angle of the first reflective member indicating a degree of variation in distance between the first reflective member and the main surface in the extending direction, and the inclination angle of the second reflective member indicating a degree of variation in distance between the second reflective member and the main surface in the extending direction.

Thus, a B-mode image includes an image of the first reflective member and an image of the second reflective member. A top-bottom direction (hereinafter referred to as a vertical direction) in the B-mode image corresponds to a direction in which the ultrasound probe transmits and receives ultrasound waves. A distance between the first reflective member image and the second reflective member image in the vertical direction (hereinafter referred to as a vertical direction distance) in the B-mode image varies according to a position of the ultrasound probe in the main surface. Thus, a position of the ultrasound probe in the main surface may be associated with the vertical direction distance between the first reflective member image and the second reflective member image in the B-mode image. With this, the position of the ultrasound probe can be precisely detected based on the vertical direction distance between the first reflective member image and the second reflective member image in the B-mode image obtained during the diagnosis. Significantly, even when a gap is present between the ultrasound probe and the main surface of the pad, the vertical direction distance between the first reflective member and the second reflective member is constant regardless of presence or absence of the gap. Thus, the position of the ultrasound probe can be precisely calculated.

For example, according to an exemplary embodiment of the present disclosure, each of the first reflective member and the second reflective member is divided into a plurality of portions by a cross-section perpendicular to the extending direction of the first reflective member, each of the portions of the first reflective member is disposed such that a distance between the portion of the first reflective member and the main surface varies in the extending direction, the portions of the first reflective member are arranged such that positional relationships of the portions of the first reflective member relative to the main surface match one another, each of the portions of the second reflective member is disposed such that a distance between the portion of the second reflective member and the main surface does not vary in the extending direction, and the portions of the second reflective member are arranged such that distances between (i) the portions of the second reflective member and (ii) the main surface are different from one another.

Thus, the B-mode image includes an image of the first reflective member and an image of the second reflective member. On which section of the pad, which is divided into sections by the cross-section perpendicular to the extending direction of the first reflective member, the ultrasound probe is placed is detected based on the position of the second reflective member image in the B-mode image. At the same time, the position of the ultrasound probe in the section is detected based on the position of the first reflective member image. Based on the detections, the position of the ultrasound probe on the pad can be precisely detected. Significantly, since the first reflective member can be disposed in a thinner pad, the thickness of the pad can be reduced. Consequently, an area in which a subject image is displayed can be increased in the B-mode image.

For example, according to an exemplary embodiment of the present disclosure, the ultrasound diagnostic adapter includes a plurality of pad sets each of which includes the pad, the first reflective member, and the second reflective member, wherein each of the first reflective members included in the pad sets is disposed such that a distance between the first reflective member and the main surface varies in the extending direction, each of the second reflective members included in the pad sets is disposed such that a distance between the second reflective member and the main surface does not vary in the extending direction, and the second reflective members included in the pad sets are arranged such that distances between (i) the second reflective members and (ii) the main surface in the extending direction are different from one another.

Thus, when a plurality of pads is used in an examination, on which pad the ultrasound probe is placed is detected based on the distance between the main surface and the second reflective member in each of the pads, and the position of the ultrasound probe on the pad is detected based on the distance between the main surface and the first reflective member. This makes it possible to precisely calculate the position of the ultrasound probe even when a plurality of pads is used in the examination.

For example, according to an exemplary embodiment of the present disclosure, the ultrasound diagnostic adapter includes a plurality of pad sets each of which includes the pad and the first reflective member, wherein the first reflective members included in the pad sets are arranged such that distances between (i) the first reflective members and (ii) the main surface are not equal to one another.

Thus, when a plurality of pads is used in an examination, on which pad the ultrasound probe is placed and where on the pad the ultrasound probe is positioned are detected based on the distance between the main surface and the first reflective member in each of the pads. This makes it possible to precisely calculate the position of the ultrasound probe even when a plurality of pads is used in the examination. Significantly, the pads each including one reflective member are used, the ultrasound diagnostic adapter can be realized with a lower cost compared to the case where pads each including more than one reflective member are used.

For example, according to an exemplary embodiment of the present disclosure, the ultrasound diagnostic adapter includes a plurality of pad sets each of which includes the pad and the first reflective member, wherein a relative position of the first reflective member to the pad as seen from the side of the main surface is different for each of the pad sets.

Thus, when a plurality of pads is used in an examination, on which pad the ultrasound probe is placed is detected based on the relative position of the first reflective member in each of the pads as seen from the main surface, and where on the pad the ultrasound probe is positioned is detected based on the distance between the main surface and the first reflective member in each of the pads. This makes it possible to precisely calculate the position of the ultrasound probe even when a plurality of pads is used in the examination. Significantly, the pads each including one reflective member are used, the ultrasound diagnostic adapter can be realized with a lower cost compared to the case where pads each including more than one reflective member are used.

For example, according to an exemplary embodiment of the present disclosure, the ultrasound diagnostic adapter further includes: a first guide rail disposed along the extending direction of the first reflective member; and a slider which holds the ultrasound probe and moves along the first guide rail.

Thus, a subject can be scanned with the ultrasound probe along the guide rail. As described, the guide rail is disposed along the extending direction of the first reflective member. Thus, in the B-mode image obtained with the above-described structure, the area in which the first reflective member image appears is limited to a certain area. Therefore, the area from which the first reflective member image is detected may be limited to the certain area. This makes it possible to more precisely and efficiently detect the first reflective member image in the B-mode image. Consequently, the position of the ultrasound probe can be precisely calculated.

For example, according to an exemplary embodiment of the present disclosure, the ultrasound diagnostic adapter further includes: two guide rails arranged along the extending direction of the first reflective member and the second reflective member; and a slider which is held between the two guide rails, the slider holding the ultrasound probe and moving along the two guide rails.

With this, when a subject is examined by scanning the subject with the ultrasound probe, the ultrasound probe can be held between and moved along the two guide rails. Therefore, the ultrasound probe can be scanned along the guide rails more precisely, and the area in which the image of the reflective member appears in the B-mode image is more precisely limited to a certain area. Therefore, it is possible to more precisely and efficiently detect the image of the reflective member in the B-mode image. Consequently, the position of the ultrasound probe can be precisely calculated.

For example, according to an exemplary embodiment of the present disclosure, the pad is disposed between the two guide rails as seen from the side of the main surface, and each of the two guide rails has a thickness greater than a thickness of the pad in a direction perpendicular to the main surface.

Thus, in the case where a force is applied to the main surface and lateral surfaces of the pad, such as when the ultrasound probe is pressed against a subject through the pad, it is possible to suppress deformation of the main surface and the lateral surfaces of the pad. This makes it possible to prevent the distance between the main surface and the reflective member from being altered. Therefore, it is possible to precisely detect the position of the ultrasound probe even when the ultrasound probe is pressed against a subject through the pad.

For example, according to an exemplary embodiment of the present disclosure, the first reflective member is disposed away from the back surface of the pad.

Thus, it is possible to prevent deformation of the reflective member even when the back surface of the pad is deformed as the ultrasound probe is pressed against a subject through the pad. Therefore, it is possible to precisely calculate the position of the ultrasound probe even when the ultrasound probe is pressed against the subject.

For example, according to an exemplary embodiment of the present disclosure, the pad includes (i) a first pad portion positioned on the side of the main surface and (ii) a second pad portion positioned on the side of the back surface, and the first reflective member is disposed inside the first pad portion.

For example, according to an exemplary embodiment of the present disclosure, the second pad portion is made from a material having a modulus of elasticity lower than a modulus of elasticity of a material included in the first pad portion.

With this, a material having a lower modulus of elasticity than a material of other portions of the pad can be pressed against a subject so as to fit to surface irregularities of the subject. This can reduce the chance that a gap is produced between the back surface of the pad and the subject. Therefore, it is possible to precisely calculate the position of the ultrasound probe even when the surface of the subject includes irregularities.

For example, according to an exemplary embodiment of the present disclosure, the pad is made from a material which has a sound velocity ranging from 1450 (m/s) to 1585 (m/s), and an average sound velocity of 1530 (m/s).

With this, a medium of the pad has acoustic characteristics about the same as acoustic characteristics of a human body. Thus, when a subject is a human body, reflection of ultrasound waves on a contact surface between the back surface of the pad and the subject can be suppressed, and a good B-mode image can be obtained. Therefore, in an ultrasound diagnose of the subject through the pad as well, the reflective member image in the B-mode image can be precisely detected, and the position of the ultrasound probe can be precisely detected.

For example, according to an exemplary embodiment of the present disclosure, a portion which is of the pad and is between the first reflective member and the main surface is made from a material having a sound velocity lower than a sound velocity of an other portion inside the pad.

With this, it is possible to reduce the velocity of ultrasound waves which travel toward the reflective member, and the velocity of reflected waves (echo) which travel toward the ultrasound probe after being reflected off the reflective member. The reflective member image in the B-mode image can be precisely obtained without increasing sampling frequency of the ultrasound probe, even when the reflective member inside the pad is present at a position rather close to the main surface. Thus, the reflective member may be disposed at a position close to the main surface, which leads to a reduction in thickness of the pad. Consequently, the area in which a subject image is displayed can be increased in the B-mode image.

In addition, an ultrasound diagnostic apparatus according to an exemplary embodiment of the present disclosure includes: the ultrasound diagnostic adapter; an ultrasound probe which transmits and receives ultrasound waves; a reflective member detection unit configured to detect, from among signals received by the ultrasound probe, a signal of reflected waves from the first reflective member; and a probe position calculation unit configured to detect, from the signal detected by the reflective member detection unit, a position of the ultrasound probe based on at least one of (i) a distance between the first reflective member and the main surface and (ii) a width of the first reflective member as seen from the side of the main surface.

Thus, the ultrasound probe can receive reflected waves (echo) from the reflective member disposed inside the pad, and an image of the reflective member appears in a B-mode image. The distance between the main surface and the reflective member, and the position of the ultrasound probe can be detected, by detecting the image of reflective member in a B-mode image. Accordingly, it is possible to precisely calculate the position of the ultrasound probe.

For example, according to an exemplary embodiment of the present disclosure, the reflective member detection unit is configured to detect a signal which is received from the pad and has an amplitude greater than or equal to a predetermined threshold from among the signals received by the ultrasound probe, as the signal from the first reflective member.

For example, according to an exemplary embodiment of the present disclosure, the reflective member detection unit is configured to detect a signal which is received from the pad and has a greatest amplitude from among the signals received by the ultrasound probe, as the signal from the first reflective member.

For example, according to an exemplary embodiment of the present disclosure, the reflective member detection unit is configured to detect a signal which is received from the pad and has a derivative value of an amplitude greater than or equal to a predetermined threshold from among the signals received by the ultrasound probe, as the signal from the first reflective member.

For example, according to an exemplary embodiment of the present disclosure, the reflective member detection unit is configured to detect a signal which is received from the pad and has a greatest derivative value of an amplitude from among the signals received by the ultrasound probe, as the signal from the first reflective member.

The reflective member image in the B-mode image can be thus detected. Accordingly, it is possible to precisely calculate the position of the ultrasound probe consequently.

For example, according to an exemplary embodiment of the present disclosure, the probe position calculation unit is configured to calculate a position of the ultrasound probe, based on at least one of (i) a distance between the first reflective member and the main surface and (ii) a width of the first reflective member as seen from the side of the main surface that are detected by the reflective member detection unit, according to a relational expression that indicates at least one of relationships of a position of the ultrasound probe to (i) a distance between the first reflective member and the main surface and (ii) a width of the first reflective member as seen from the side of the main surface that are detected by the reflective member detection unit.

With this, the position of the ultrasound probe can be calculated easily based on the distance between the main surface and the reflective member obtained from the B-mode image. Thus, it is possible to precisely calculate the position of the ultrasound probe based on the information detected from the information included in the B-mode image.

For example, according to an exemplary embodiment of the present disclosure, the probe position calculation unit is configured to calibrate the relational expression using at least one of (i) a distance between the first reflective member and the main surface and (ii) a width of the first reflective member as seen from the side of the main surface that are detected between when the ultrasound probe is disposed at a first predetermined position and when the ultrasound probe is moved to a second predetermined position that is different from the first predetermined position.

With this, it is possible to construct the relational expression using a pad which is actually used in the ultrasound diagnosis. This makes it possible to further reduce a measurement error that may exist and vary for each pad. Consequently, it is possible to precisely calculate the position of the ultrasound probe.

For example, according to an exemplary embodiment of the present disclosure, the probe position calculation unit is further configured to detect positions of the first reflective member obtained over a course of time and calculate an amount of movement between the positions of the ultrasound probe.

With this, it is possible to calculate not only the position of the ultrasound probe on the pad but also the distance traveled by the ultrasound probe in a time period from a reference measurement time to a time of diagnosis. Accordingly, the distance traveled by the ultrasound probe in a certain period of time can be precisely calculated.

Note that the exemplary embodiments of the present disclosure can be realized not only as the ultrasound diagnostic apparatus, but also as: a method which includes, as steps, the processing means included in the ultrasound diagnostic apparatus; a program which causes a computer to execute such steps; a recording medium such as a computer-readable CD-ROM having the program recorded thereon; and information, data or signals that represent the program. In addition, such program, information, data, and signals may be distributed via a communication network such as the Internet.

Hereinafter, certain exemplary embodiments of the present disclosure are described in greater detail with reference to the accompanying Drawings.

Each of the exemplary embodiments described below shows a general or specific example. The numerical values, shapes, materials, structural elements, the arrangement and connection of the structural elements, steps, the processing order of the steps etc. shown in the following exemplary embodiments are mere examples, and therefore do not limit the inventive concept. Therefore, among the structural elements in the following exemplary embodiments, structural elements not recited in any one of the independent claims defining the most generic part of the inventive concept are described as optional structural elements.

Embodiment 1

Figure 1:
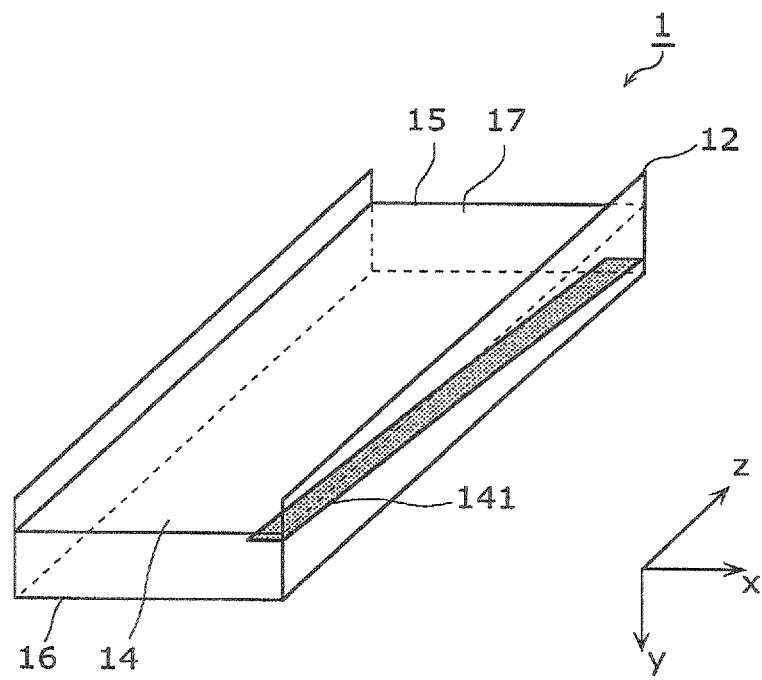
FIG. 1 is an outline view of an ultrasound diagnostic adapter according to Embodiment 1.

FIG. 1 shows an example of an ultrasound diagnostic adapter according to this embodiment. The ultrasound diagnostic adapter 1 is disposed between an ultrasound probe of the ultrasound diagnostic apparatus and a body surface (subject) over a site of interest. The ultrasound diagnostic adapter 1 includes a pad 14 and a reflective member. The reflective member is disposed inside the pad 14, and includes a material having a different acoustic impedance than a material of the pad. The pad is made from a member that can be easily fit to a curved shape of the subject (e.g., polymer gel). On the other hand, the reflective member is made of, for example, a material such as aluminum or stainless steel. Note that the reflective member is made from, for example, a material which does not corrode even when disposed inside the pad for a long time. In addition, for example, the pad is made from a material which has a sound velocity ranging from 1450 (m/s) to 1585 (m/s), and an average sound velocity of 1530 (m/s). With this, a medium of the pad has acoustic characteristics about the same as acoustic characteristics of a human body. Thus, when a subject is a human body, reflection of ultrasound waves on a contact surface between the back surface of the pad and the subject can be suppressed.

Here, a surface of the pad 14 where the ultrasound probe is disposed is referred to as a main surface 15, and the surface opposite to the main surface 15 is referred to as a back surface 16. When a diagnosis is made, the back surface 16 is in contact with the subject, and ultrasound waves are transmitted toward the back surface side (subject side) from the main surface side. Note that, in FIG. 1, a scan area 17 shows a portion or all of the area in the main surface 15 scanned by the ultrasound probe.

Note that, as shown in FIG. 1, the direction perpendicular to the main surface 15 shall be a y-direction, the direction in which the reflective member extends shall be a z-direction, and the direction orthogonal to the y-direction and the z-direction shall be an x-direction. Orientation of each of the directions shall be as shown in the drawing. The same coordinate system is also used in other drawings.

Figure 2:
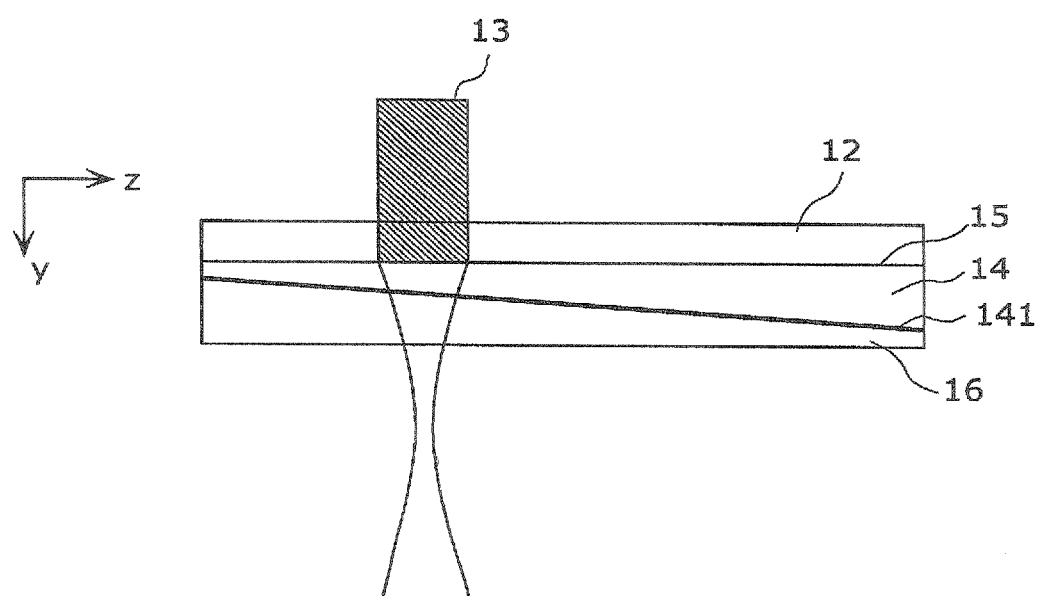
FIG. 2 is a lateral view of the ultrasound diagnostic adapter according to Embodiment 1.

FIG. 2 is a lateral view of the ultrasound diagnostic adapter 1 according to this embodiment. The ultrasound diagnostic adapter 1 includes inside the pad 14 a reflective member 141. The reflective member 141 runs through a portion of the scan area 17. The reflective member 141 is disposed at an angle greater than 0 degrees to the main surface 15. The distance between the main surface and the reflective member is different depending on the position in the main surface of the pad. The reflective member 141 is disposed such that the distance between the reflective member 141 and the main surface 15 gradually increases as the position in the pad progresses in the z-direction in FIG. 2.

In FIG. 1 and FIG. 2, the reflective member 141 is substantially linear, and the extending direction (the z-direction) of the reflective member as seen from the main surface 15 side is parallel to the scan direction of the ultrasound probe. In addition, in rectangular parallelepiped scan area, the reflective member 141 is disposed so as to extend along one of the sides parallel to the scan direction of the ultrasound probe.

Figure 3:
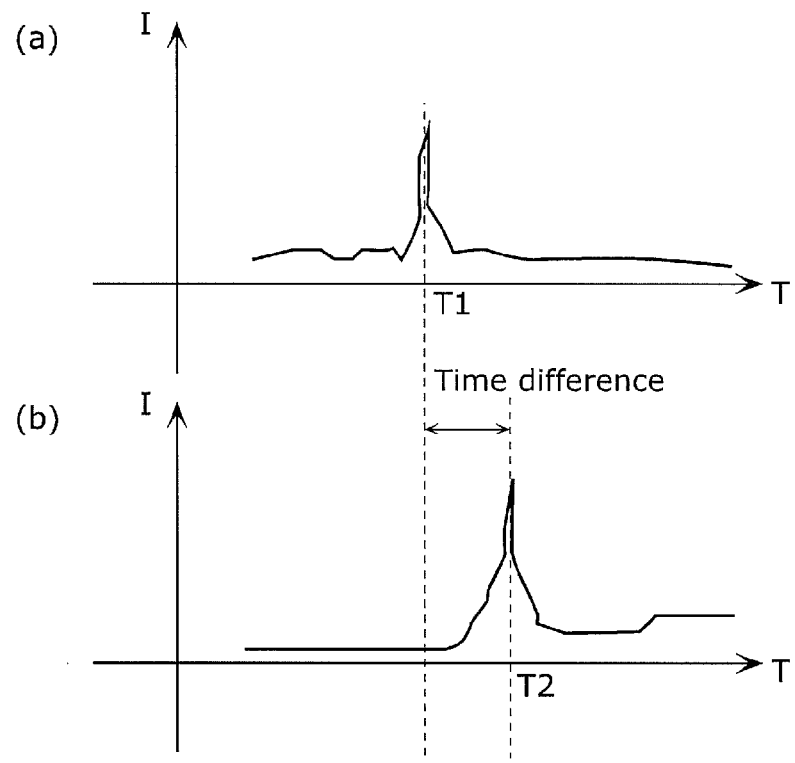
FIGS. 3(a) and (b) are graphs showing reflected waves of ultrasound (echo) obtained using the ultrasound diagnostic adapter.

Echoes received by the ultrasound probe 13 in the cases where distances between the reflective member 141 and the main surface 15 are different is described with reference to FIG. 3. In FIG. 3, the horizontal axis represents a time t (horizontal axis) from the time when the ultrasound probe transmits an ultrasound pulse to when the ultrasound probe receives the echo, and the vertical axis represents intensity (amplitude) I of the received echo. Shown in (a) and (b) in FIG. 3 are examples of echoes received at sites of which z-coordinate are z1 and z2, respectively (note that the sites are within the area where echoes from the reflective member 141 are received). Here, it is assumed that the distance between the reflective member 141 and the main surface 15 at the z2 point is greater than the distance between the reflective member 141 and the main surface 15 at the z1 point. Since the acoustic impedance of the reflective member is different from the acoustic impedance of the material included in the pad, the reflective member shows different reflectance characteristics on the ultrasound waves. Thus, after the ultrasound probe transmits ultrasound waves toward the inside of a body, the ultrasound probe receives an echo from the reflective member in addition to an echo from the inside of the body.

Note that, in this embodiment, it is assumed that the acoustic impedance of the reflective member 141 is greater than the acoustic impedance of the pad 14, and the amplitude intensity of the echo from the reflective member 141 is detected to be greater than the echo from the subject. In (a) and (b) in FIG. 3, the time-t taken to receive the echo from the reflective member 141 are different. This is because the distances between the reflective member 141 and the main surface are different. Taking advantage of the fact that the period of time from when the ultrasound probe transmits the ultrasound waves to when the echo from the reflective member 141 is detected is different depending on the position of the ultrasound probe, the ultrasound diagnostic apparatus can calculate the position of the ultrasound probe at the point of time when the B-mode image is obtained or relative positional relationships among the B-mode images.

As described, the reflective member is disposed inside the pad such that the distance between the main surface of the pad and the reflective member is different depending on the position in the main surface of the pad. With this, the position of the ultrasound probe in the main surface and the relative positional relationships among the B-mode images can be easily detected. Furthermore, different from the conventional method in which the position of the ultrasound probe is determined based on the correlations among the images, the method according to this embodiment does not use image states showing composition distribution inside a body to detect the position of the ultrasound probe. Thus, the position of the ultrasound probe can be detected accurately without depending on the composition distribution inside a body and a scan rate of the ultrasound probe.

Note that it is possible to specifically detect the position of the ultrasound probe and calculate the relative position of the obtained B-mode images, using the ultrasound diagnostic adapter 1 according to this embodiment. The methods of detecting the position of the ultrasound probe and calculating the relative positional information are described later.

Note that the reflective member according to this embodiment may be disposed at any position inside the pad. For example, the reflective member is disposed so as not to be in contact with the back surface of the pad (the surface which contacts the subject). In other words, for example, the point of the reflective member closest to the subject is present at the position at a predetermined distance away from the back surface of the pad. As the ultrasound probe is pressed against a human body through the pad, the shape of the back surface of the pad changes according to the shape of the subject. Then, if the reflective member is disposed such that a portion of the reflective member is in contact with the back surface of the pad, the shape of the reflective member may be greatly influenced by the deformation of the pad and deformed. In view of this, the reflective member may be disposed at the position predetermined distance apart from the back surface of the pad. With this, the influence on the reflective member caused by the deformation of the pad can be reduced and the position of the ultrasound probe can be detected more accurately. For example, an experiment performed on a polymer gel shows that the deformation of the reflective member 141 is reduced to a level that does not affect in making observations, when the reflective member 141 is spaced apart from the back surface 16 by 5 mm to 10 mm.

In other words, when the pad includes a first pad portion positioned on the side of the main surface and a second pad portion positioned on the side of the back surface, and the thickness of the second pad portion positioned on the side of the back surface (subject side) is from 5 mm to 10 mm, the deformation of the reflective member 141 is successfully reduced. Note that the reflective member is disposed in the first pad portion. Note that, although the pad is referred to as the first pad portion and the second pad portion for reasons of expediency, it is apparent that the first pad portion and the second pad portion do not necessarily have to be separate portions but may be integrated with each other. The first pad portion and the second pad portion that are integrated with each other allows for reduction of noise, because unwanted reflection does not occur at the interface between the two pads.

In addition, the pads may also include at least two types of materials. In other words, in the pad, a second substance is used for the side which is pressed against the body surface, and a first substance having a higher hardness than the second substance is used for an area which is closer to the ultrasound probe than the area for which the second substance is used. The reflective member is disposed in the first substance having the high hardness. In the above-described example, the second substance is used for the second pad portion, and the first substance is used for the first pad portion. For example, materials of the first substance and the second substance may be aqueous gels, taking into account the aforementioned constraint on the sound velocity, and have different hardness. However, the materials of the first and second substances are not limited to the aqueous gel.

When the first substance and the second substance having mutually different hardness are used, each substance can fulfill a different function, that is, a fitting function for conforming to the shape of the subject and a function for reducing deformation of the portion between the reflective member and ultrasound probe. Specifically, a material having a relatively low hardness is used as the second substance. With this, a shape of the back surface of the pad can be changed to conform to the shape of the subject. On the other hand, a material having a relatively high hardness is used for the first substance that is used on the side far from the subject. With this, the shape of the reflective member disposed in the first substance or the distance between the main surface and the reflective member is not likely to be affected even when the pad is deformed as the ultrasound probe is pressed against the body surface. This makes it possible to reduce errors which occur during detection of positions.

Note that the reflective member 141 may be disposed at any position as long as the position is included in the scan area of the ultrasound probe. When the reflective member is disposed on the edge of the scan area as described above, the reflective member image appears on the edge of the B-mode image to be obtained. Thus, an area corresponding to the subject in the B-mode image is not divided. Furthermore, even when the reflective member is disposed such that the reflective member image appears on the position other than the edge of the B-mode image, e.g., the reflective member is disposed on the center of the scan area of the ultrasound probe, the advantageous effects are produced that the position of the ultrasound probe or the relative positions of the obtained B-mode images can be detected.

Furthermore, the reflective member 141 may be in any shape. For example, the reflective member 141 may be in a linear shape. The reflective member 141 does not necessarily have to be parallel to one side of the scan area as seen from the main surface side. For example, when the reflective member 141 has a serpentine shape as seen from the main surface 15 side, the piezoelectric element, among piezoelectric elements (ultrasound transducers) included in the ultrasound probe 13, which detects the echo from the reflective member 141 can vary depending on the position of the ultrasound probe 13 in the main surface. This complicates a step for extracting a signal of the reflective member 141 from the detected signals. In this case, too, it is possible to obtain the position of the ultrasound probe and relative positional relationships among the B-mode images. However, for example, when the reflective member 141 is linear shaped, the distance between the main surface and the reflective member 141 varies monotonically. With this, the step for obtaining the position of the ultrasound probe is simpler.

Furthermore, for example, the reflective member 141 may have a linear shape in a cross-section of the reflective member in the yz-plane in FIG. 1, too. For example, in the case where the reflective member 141 has a serpentine shape in the cross-section of the reflective member in the yz-plane, too, the ultrasound diagnostic apparatus may store in advance a look-up table (LUT) which indicates relation between the shape of the reflective member 141 and the time taken to detect the reflective member 141, as described later. The position of the ultrasound probe can be obtained based on the LUT. However, there may be positions at which the distance between the reflective member 141 and the main surface 15 are the same in the serpentine-shaped reflective member. Thus, to allow the step for obtaining the position of the ultrasound probe to be simple, the reflective member 141 may be, for example, linear-shaped.

Furthermore, although FIG. 1 and FIG. 2 show an embodiment in which one reflective member 141 is disposed in the scan area of the ultrasound probe, two or more reflective members 141 may be disposed in the scan area. Such embodiments will be described later.

Note that the reflective member 141 is not limited to a single member but may be formed of members of predetermined lengths arranged intermittently at a predetermined interval.

Furthermore, the reflective member in the above embodiment may include a material which has properties to absorb ultrasound waves (absorbent). When the reflective member includes an absorbent, the ultrasound diagnostic adapter 1 can avoid multiple reflections between the reflective member and the ultrasound probe. An example of a material of an absorbent includes, but not limited to, a cyst.

Note that, when scanning the ultrasound probe on the pad, an operator moves the ultrasound probe so as to pass over the area where the reflective member 141 is disposed in the pad. At this time, the operator may move the ultrasound probe on the pad freehand. However, with an after-mentioned scan assist mechanism, the ultrasound probe can be moved more linearly.

The following describes the scan assist mechanism for moving the ultrasound probe linearly when the ultrasound probe is moved in the main surface of the pad.

Figure 4:
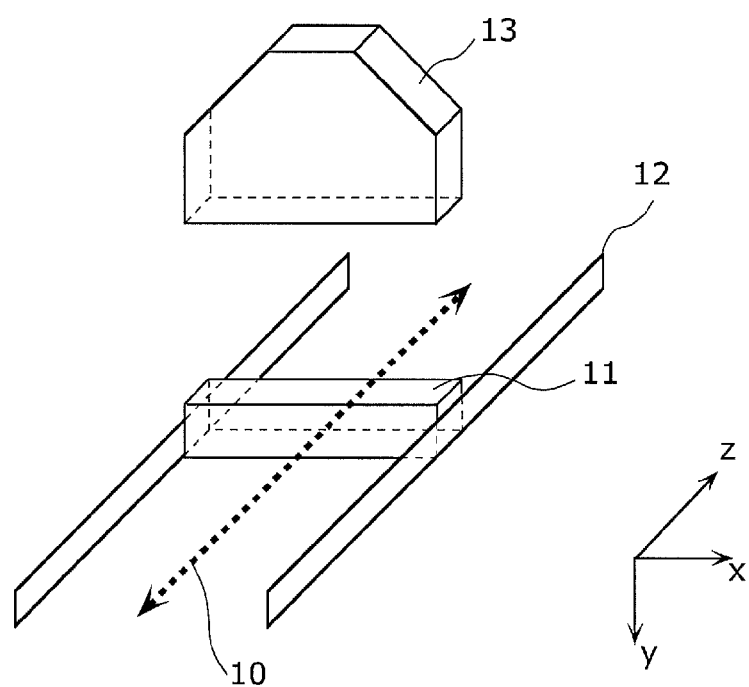
FIG. 4 is an outline view of a scan assist mechanism of an ultrasound probe.
Figure 5:
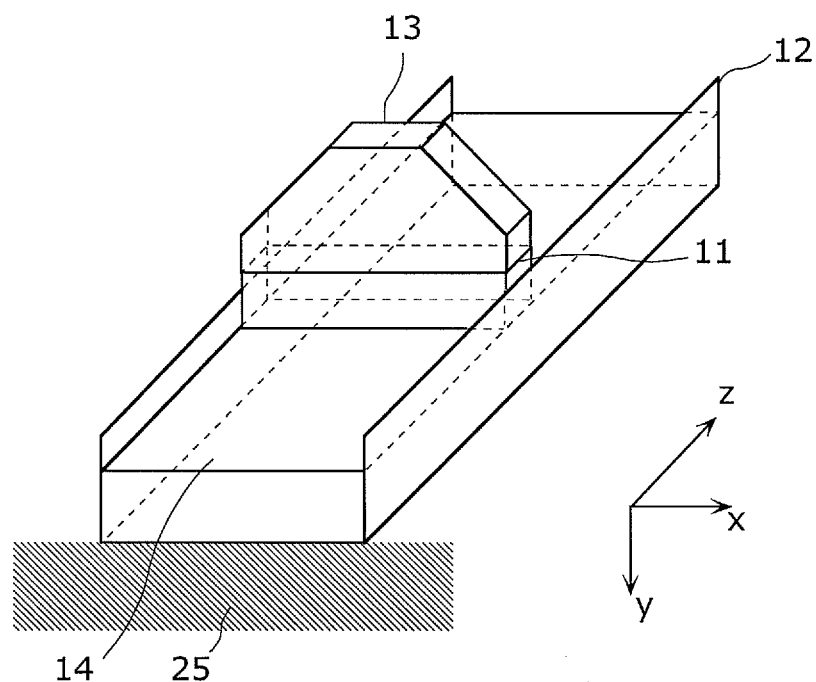
FIG. 5 is an outline view showing the ultrasound diagnostic adapter combined with the scan assist mechanism of the ultrasound probe.

FIG. 4 shows an example of the scan assist mechanism for moving the ultrasound probe 13 linearly. The scan assist mechanism includes at least: two guide rails 12 arranged along the extending direction of the reflective member; and a slider 11 disposed between the guide rails 12. Each of the guide rails 12 is, as shown in FIG. 5, formed on the main surface of the pad 14, and arranged on the main surface along the direction in which the ultrasound probe is to be moved (scan direction). Note that the pad may be integrated in the scan assist mechanism from the beginning or the scan assist mechanism may be disposed separately from the pad.

The slider 11 can hold the ultrasound probe 13. For example, the operator combines the slider 11 and the ultrasound probe 13 by inserting the ultrasound probe 13 to the slider 11. The slider 11 is formed such that the slider 11 can move along the guide rails 12. For example, the ultrasound probe 13 and the slider 11 can be moved along a scan direction 10 of the ultrasound probe shown by the dotted line in FIG. 4. Since the slider 11 moves along the guide rails 12, the operator can move the ultrasound probe 13 more linearly compared to the case where the operator moves the ultrasound probe 13 freehand. With this, the B-mode images of a site of interest to be displayed in three-dimension can be obtained.

Note that, in FIG. 4, two guide rails 12 that are parallel to each other are disposed on the main surface of the pad. Even with one guide rail 12, the slider 11 can be moved along the guide rail 12 by pressing the slider 11 against the guide rail 12 (or creating a mechanism that prevents the slider 11 from moving away from the guide rail 12). When two guide rails 12 are provided, each of the ends of the slider 11 is supported by the guide rail 12, and thus the ultrasound probe can be moved along the guide rail 12 more precisely. Note that the above-described scan assist mechanism is optional if the ultrasound probe can be moved in a predetermined direction.

Furthermore, the scan assist mechanism may include three or more guide rails 12 that are arranged in parallel. Such a structure makes it possible to enlarge the area on which the ultrasound probe can be moved along the guide rail.

Note that the ultrasound diagnostic apparatus obtains the B-mode images while moving the ultrasound probe 13, which is held by the slider 11, along the guide rail 12. Then, the ultrasound diagnostic apparatus combines B-mode images so as to produce a three-dimensional image of a site of interest.

Figure 6:
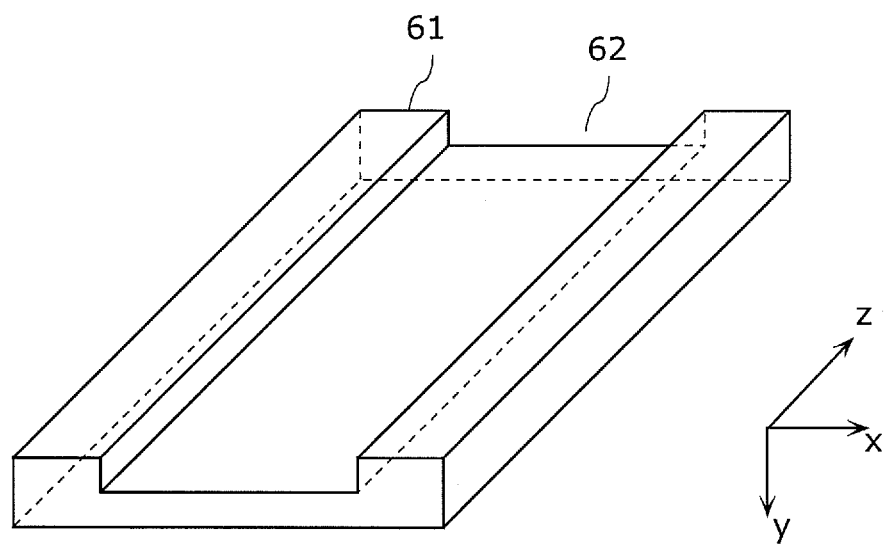
FIG. 6 is an outline view for describing an example of the scan assist mechanism of the ultrasound probe.

Note that, although the scan assist mechanism in this embodiment has a structure shown in FIG. 4, the scan assist mechanism is by no means limited to the structure shown in FIG. 4. For example, FIG. 6 shows an example of a structure in which a recess 62 is provided on a pad 61 to assist the movement of the ultrasound probe, instead of the structure in which the guide rail is attached to the pad. This structure also allows the ultrasound probe to be moved along the recess 62. Since the guide rail and the pad are integral, position adjustment between the guide rail and the pad is unnecessary. Note that an illustration of the reflective member is omitted in FIG. 6.

Further, the guide rail may be separated from the pad as long as the guide rail is disposed along the extending direction of the reflective member. This is because, as long as the reflective member according to this embodiment is disposed inside the pad, the position of the ultrasound probe can be detected by moving the ultrasound probe along the reflective member, even if the pad and the guide rail are separated. In addition, it is apparent that the structure in which the ultrasound probe and the pad are separated is also acceptable.

Figure 7:
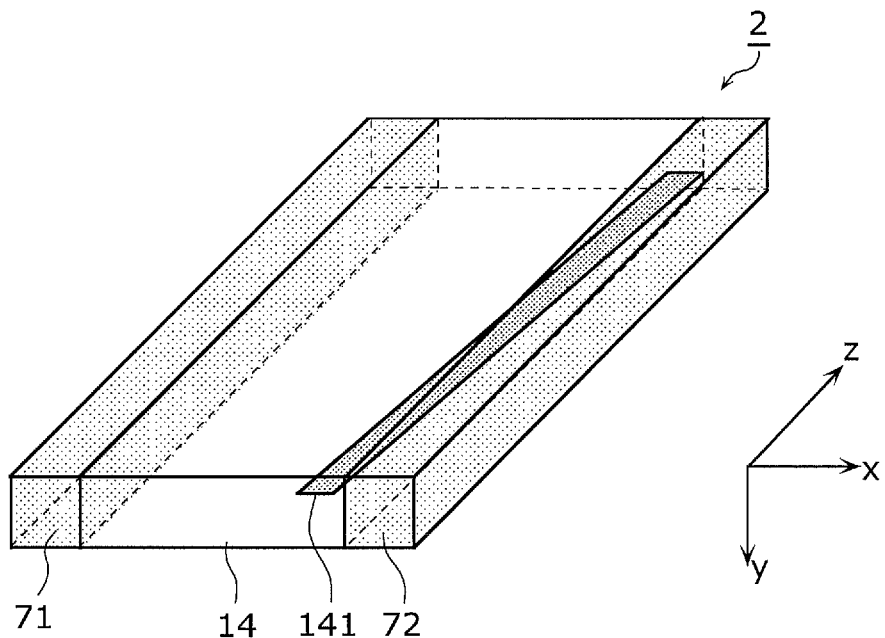
FIG. 7 is an outline view for describing an example of guide rails of an ultrasound diagnostic adapter.

Furthermore, the ultrasound diagnostic adapter may use a guide rail which (i) includes a material having a higher hardness than the pad, (ii) has a thickness greater than or equal to the thickness of the pad, and (iii) is disposed on a lateral side of the pad. An example of such a structure is shown in FIG. 7 as an ultrasound diagnostic adapter 2. With this structure, in the case where a force is applied to the main surface and lateral surfaces of the pad such as when the ultrasound probe is pushed onto a subject through the pad, it is possible to suppress deformation of the main surface and the lateral surfaces of the pad. This makes it possible to prevent deformation of the reflective member disposed inside the pad.

Embodiment 2

This embodiment is characterized in that the ultrasound diagnostic apparatus can calculate the position of the ultrasound probe by using the pad in which the aforementioned reflective member is disposed, and detecting an image of the reflective member from the B-mode image which includes images of the pad and a subject.

In the following, description is given of an example of a three-dimensional image displaying mechanism which produces a three-dimensional image based on a plurality of B-mode images.

Figure 8:
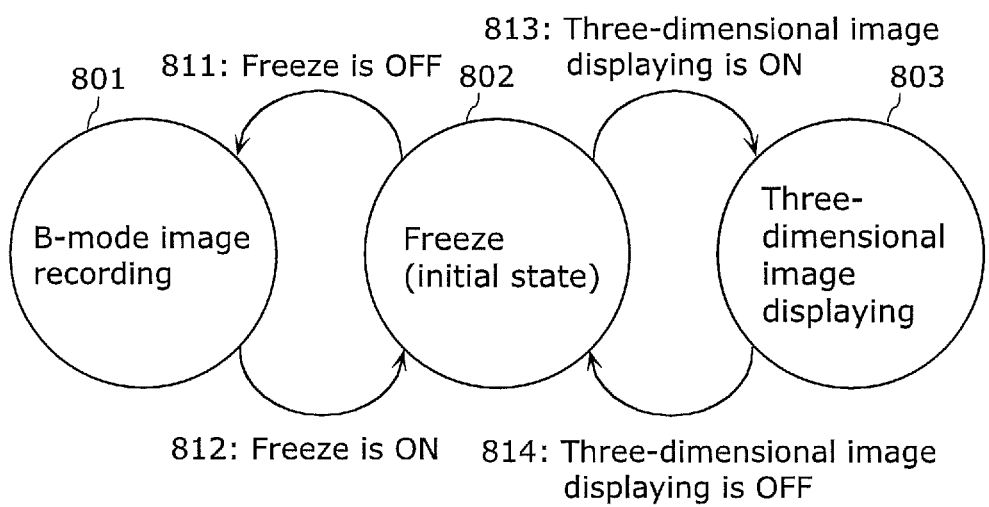
FIG. 8 is a diagram which describes operations of an ultrasound diagnostic adapter according to Embodiment 2.

First, an operation overview of a three-dimensional image displaying mechanism according to this embodiment is described with reference to a state change diagram in FIG. 8. The initial state is a freeze mode (802). In this state, ultrasound waves are not transmitted from the ultrasound probe. Then, when the operator unlocks the freeze state (811: freeze is OFF), the mode is changed to a B-mode image recording mode (801) in which a B-mode image can be recorded. In the B-mode image recording mode, the operator moves the ultrasound probe integral with the slider to obtain the B-mode images.

After obtaining the B-mode images, the mode is returned to the freeze mode (812: freeze is ON). Next, when the mode is switched to a three-dimensional image displaying mode (803) (813: three-dimensional image displaying is ON), a three-dimensional image is produced.

Figure 9:
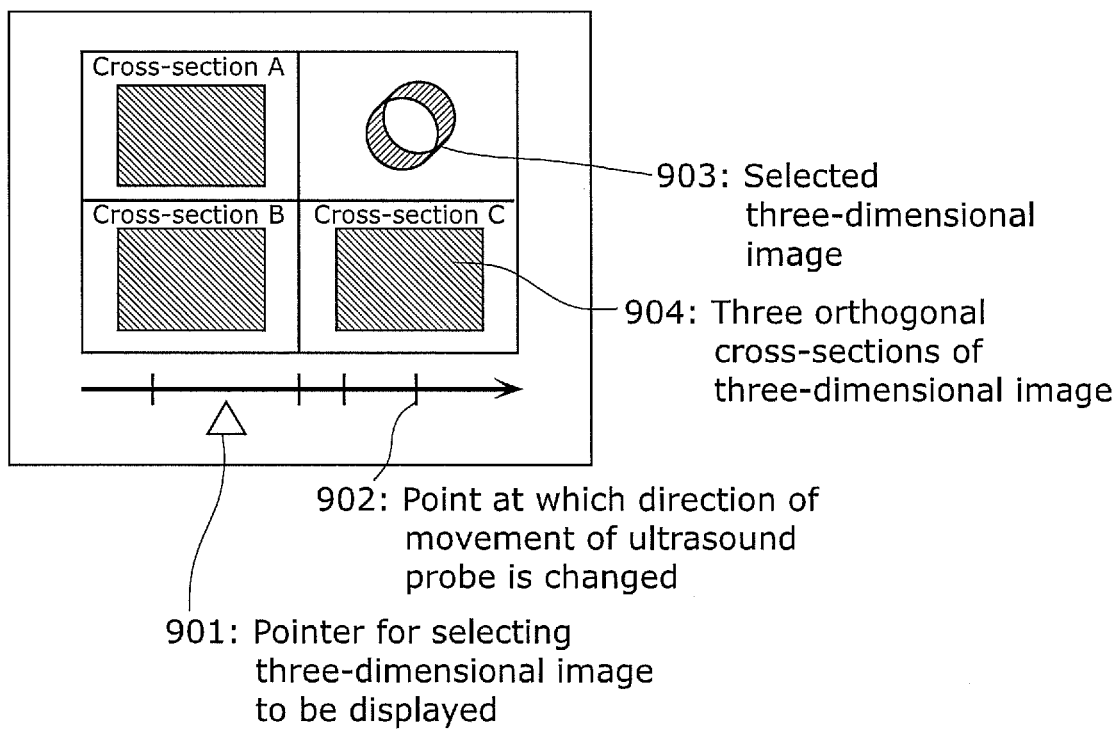
FIG. 9 is a diagram showing an example of displaying a three-dimensional image.

When the same subject is scanned with the ultrasound probe more than once such as the case where the ultrasound probe is reciprocated, the B-mode images, which are enough to produce the same number of three-dimensional images as the number of times scans are performed, can be obtained. For example, an interval between scans is detected from a movement history of the ultrasound probe so that the three-dimensional image is produced every time the interval occurs. Specifically, when the ultrasound probe is reciprocated once, two three-dimensional images are produced. When three-dimensional images are produced, the operator selects, for example, the three-dimensional image desired to be displayed on the operation screen as shown in FIG. 9. After finishing the confirmation of the three-dimensional image, the mode is returned to the freeze mode (802) (814: three-dimensional image displaying is OFF).

Next, a functional block of an ultrasound diagnostic apparatus according to this embodiment is described with reference to FIG. 10.

The ultrasound diagnostic apparatus includes: an ultrasound transmitting and receiving unit 1001 which transmits and receives ultrasound waves, a tomographic image producing unit 1002 which produces a B-mode image based on the received echo, a reflective member detection unit 1003 which detect an reflective member image in the B-mode image, an unnecessary area removing unit 1004 which removes un unnecessary area from the B-mode image, a probe position calculation unit 1005 which calculates the position of the ultrasound probe based on the position of the reflective member, a tomographic image memory unit 1006 which records B-mode images, a three-dimensional image producing unit 1007 which produces a three-dimensional image based on the recorded B-mode images, and a display unit 1008 which displays, for example, the B-mode image and the three-dimensional image.

The following describes a flow of data.

The ultrasound transmitting and receiving unit 1001 transmits ultrasound waves to a subject through the pad in which the reflective member is disposed, and receives an echo, and converts the received echo into a corresponding echo signal. Then, the ultrasound transmitting and receiving unit 1001 outputs an echo signal D1011 to the tomographic image producing unit 1002.

The tomographic image producing unit 1002 receives the echo signal D1011, which is outputted from the ultrasound transmitting and receiving unit 1001, and produces a B-mode image by converting the echo signal into a brightness value. Then, the tomographic image producing unit 1002 outputs to the reflective member detection unit 1003 and the unnecessary area removing unit 1004 a B-mode image D1012 that is produced.

The reflective member detection unit 1003 receives the B-mode image D1012, which is outputted from the tomographic image producing unit 1002, performs after-mentioned image processing to detect an image of the reflective member in the B-mode image and calculate the position in the vertical direction corresponding to a coordinate of the image in the vertical direction position. Then, the reflective member detection unit 1003 outputs vertical direction positional information D1013 of the reflective member to the probe position calculation unit 1005.

The unnecessary area removing unit 1004 receives the B-mode image D1012, which is outputted from the tomographic image producing unit 1002, and removes from the B-mode image an area which includes a pad image and the reflective member image that are unnecessary for making a diagnosis. Then, the unnecessary area removing unit 1004 outputs a B-mode image D1014, which is the B-mode image from which the unnecessary area is already removed, to the tomographic image memory unit 1006 and the display unit 1008.

The probe position calculation unit 1005 calculates, based on the vertical direction positional information D1013 of the reflective member which is outputted from the reflective member detection unit 1003, positional information D1015 of the ultrasound probe at the point of time when the B-mode image was obtained. Then, the probe position calculation unit 1005 outputs the calculated positional information of the ultrasound probe to the tomographic image memory unit 1006. Note that the unnecessary area removing unit 1004 is optional if the image to be displayed may include the reflective member image. Furthermore, the unnecessary area removing unit 1004 may not be needed, and a predetermined area out of the three-dimensional image produced by the after-mentioned three-dimensional image producing unit 1007 may be selected and transmitted to the display unit 1008.

The tomographic image memory unit 1006 is a storage device in which the B-mode image D1014, which is the output from the unnecessary area removing unit 1004, and the positional information D1015 of the ultrasound probe, which is the output from the probe position calculation unit 1005, are recorded.

The three-dimensional image producing unit 1007 produces the three-dimensional image by reading the positional information D1015 of the ultrasound probe corresponding to the B-mode images D1014 recorded in the tomographic image memory unit 1006, and arranging the B-mode images based on the positional information. Then, the three-dimensional image producing unit 1007 outputs the produced three-dimensional image D1017 to the display unit 1008.

The display unit 1008 receives and displays, on a display apparatus such as a display, the B-mode image, which is outputted from the unnecessary area removing unit 1004, and the three-dimensional image D1017, which is outputted from the three-dimensional image producing unit 1007.

Figure 10:
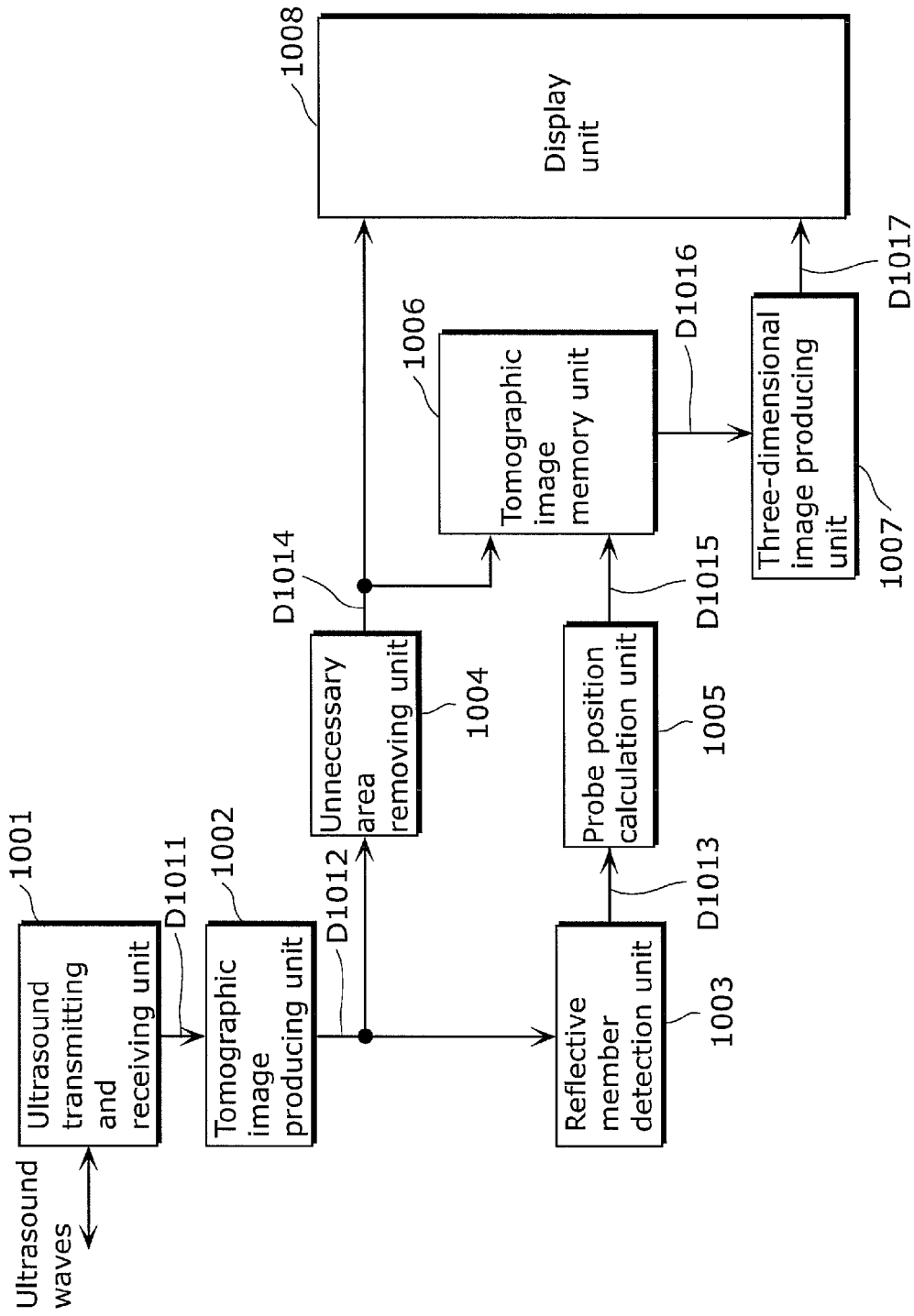
FIG. 10 shows a functional block diagram of an ultrasound diagnostic apparatus according to Embodiment 2.

Note that, although the ultrasound transmitting and receiving unit 1001 in FIG. 10 corresponds to the ultrasound probe, the ultrasound probe may be configured to include a part of or all of the other functional blocks 1002 to 1008.

Note that the functional blocks 1002 to 1005 and 1007 may be implemented in software such as a CPU, a memory, and a program or in hardware such as a dedicated electronic circuit.

This concludes the description of the functional blocks of the ultrasound diagnostic apparatus.

Figure 11:
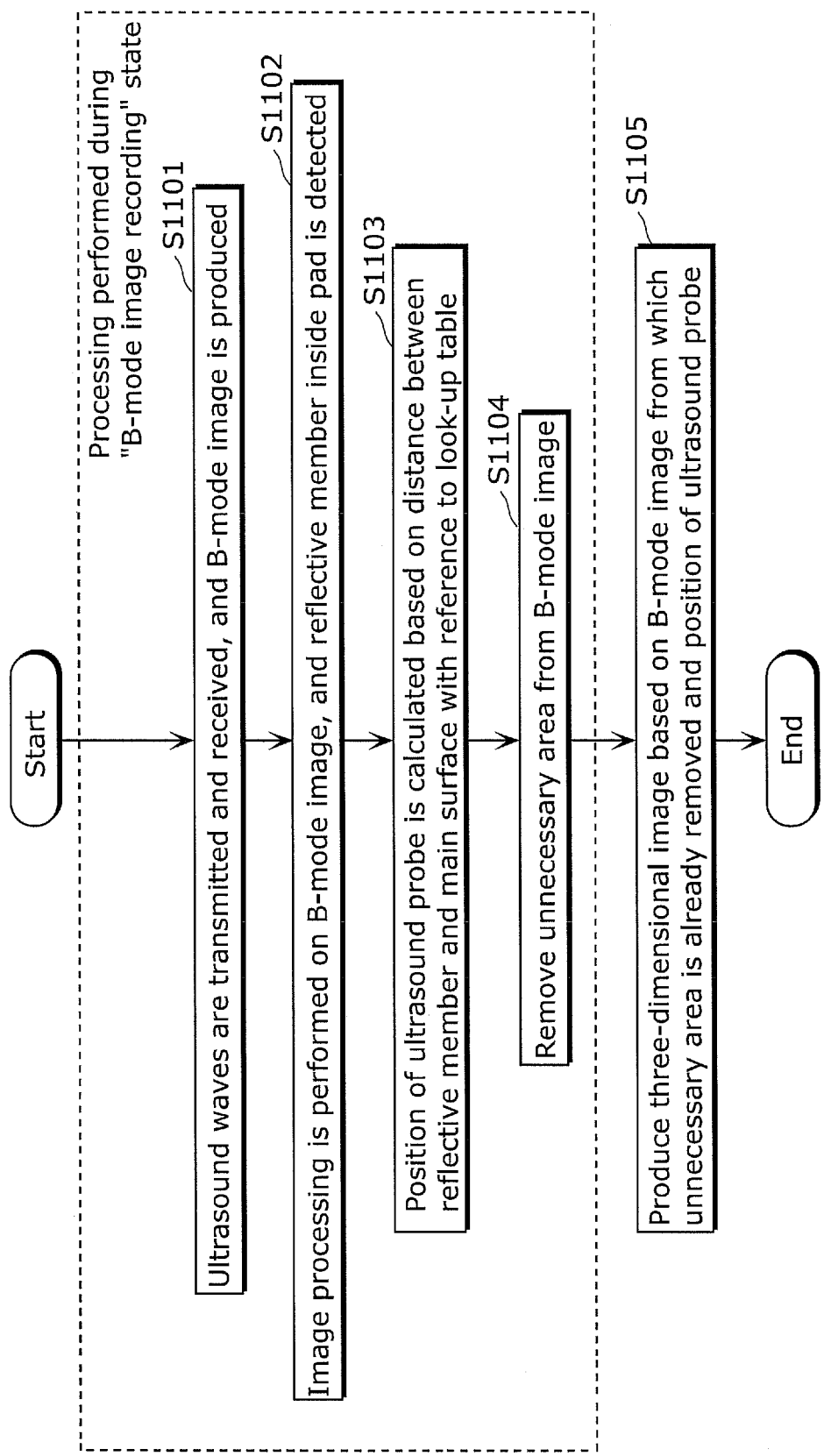
FIG. 11 is a diagram which describes operations of a three-dimensional image displaying mechanism according to Embodiment 2.

Next, a flow of operations of the ultrasound diagnostic apparatus according to this embodiment is described with reference to a flowchart in FIG. 11 and the B-mode images shown in FIG. 12.

In preparation for a scan, the operator sets the ultrasound probe 13 to the slider 11 as shown in FIG. 5. Then, the operator places the pad on a body surface over a site of interest to be displayed in three-dimension. Then, the operator unlocks the freeze state, and start moving the ultrasound probe together with the slider.

In the ultrasound diagnostic apparatus, in Step S1101, the ultrasound transmitting and receiving unit 1001 transmits ultrasound waves from the ultrasound probe, and receives an echo from the inside of the body of the subject in a line-by-line manner. Further, the tomographic image producing unit 1002 converts the received echo (echo from the subject) of each line into a brightness value by performing processing such as envelope detection, logarithmic compression, and the like to produce the B-mode image.

Next, in Step S1102, the reflective member detection unit 1003 detects the reflective member image in the B-mode image. In (*a*) in FIG. 12, an example of a B-mode image is shown. In the B-mode image, a pad area that is an area in which the pad image is shown is positioned at the upper area (1201) of the B-mode image, and a subject area in which information obtained from the subject in contact with the back surface of the pad is shown is positioned in the area (1202) below the pad area. Here, the pad includes the reflective member having a different acoustic impedance than a material included in the pad, and a signal from the reflective member appears as a high brightness area (1203) in a B-mode image. Here, the reflective member detection unit 1003 detects the high brightness area (echo from the reflective member) in a B-mode image, and the probe position calculation unit 1005 calculates the position of the ultrasound probe based on the position of the high brightness area.

The reflective member detection unit 1003, for example, limits the area from which the reflective member image is detected to the reflective member detecting area (1204) that is an edge of the pad, and performs edge detection in a line-by-line manner, and thus detects the position of the reflective member image. Specifically, a portion having the highest derivative value of brightness with respect to a variation in the vertical direction in the reflective member detecting area is detected as the reflective member image.

FIG. 13 shows an enlarged view of the reflective member detecting area in a B-mode image. In FIG. 13, a reflective member image 1302 is shown as a white rectangle. The reflective member detection unit 1003 detects, as the reflective member image, a portion (1301) having the highest derivative value of brightness with respect to a variation in the vertical direction. Here, the distance between the main surface and the reflective member corresponds to the number of pixels (1303) between the reflective member image and the top of the B-mode image shown in FIG. 13.

Further, in Step S1103, the probe position calculation unit 1005 calculates based on the position of the detected reflective member the position of the ultrasound probe at the point of time when the B-mode image was obtained. For the calculation, a look-up table 1401 and the like shown in FIG. 14 is used. In the look-up table 1401, the number of pixels between the top of a B-mode image and an image of the reflective member is associated in a one-to-one correspondence with the position of the ultrasound probe. For example, it is assumed that the reference position is the position of the ultrasound probe at the time when the reflective member image obtained by the reflective member detection unit 1003 is 5 pixels away from the top of a B-mode image. Then, if the reflective member image is 7 pixels away from the top, the ultrasound probe is located at the position 10 mm away from the reference position.

The look-up table 1401 is reconfigurable. The reconfiguration is possible by, for example, disposing the ultrasound probe at a predetermined position, and associating the position of the ultrasound probe and the position of the reflective member image in the vertical direction. Specifically, as shown in FIG. 16, the number of pixels "a" between the top and the reflective member in the B-mode image when the ultrasound probe is placed at the position A, and the number of pixels "b" between the top and the reflective member in the B-mode image when the ultrasound probe is placed at the position B are used to obtain a line that passes the point (a, A) and the point (b, B). The line equation means the relational expression between the position of the reflective member image in the vertical direction and the position of the ultrasound probe. The look-up table 1401 is re-generated based on the relational expression. It is apparent that the position of the ultrasound probe may be directly calculated using the line equation.

Next, in Step S1104, in order to extract from the B-mode image a subject area to be used for making a diagnosis, the unnecessary area removing unit 1004 removes a removal area (1205). The removal area (1205) is the pad area and the area showing the reflective member image in the B-mode image. In (*b*) in FIG. 12, an example of the removal area is shown.

The above-described processing in Step S1101 to Step S1104 is performed in the state where the freeze is unlocked. The B-mode image from which the unnecessary area is already removed and the positional information of the ultrasound probe are associated and recorded in the tomographic image memory unit 1006.

After the B-mode images of the site of interest to be displayed in three-dimension are obtained, the operator sets the ultrasound diagnostic apparatus to the freeze mode, and then changes the mode to the three-dimensional image displaying mode. Then, in Step S1105, the three-dimensional image producing unit 1007 produces a three-dimensional image by reading the B-mode image and the positional information of the ultrasound probe recorded in the tomographic image memory unit 1006, and setting the brightness value of the B-mode image to a corresponding voxel in a three-dimensional space. FIG. 15 shows an example of a produced three-dimensional image. A brightness value is determined by an interpolation from the neighboring voxels, if there is a voxel to which brightness is not set due to timing when the B-mode image is obtained, timing when the scan is started and ended, a change in scan rate, or the like.

This concludes the description on the flow of operations.

Different from the conventional technique, the structure described above does not need expensive position sensors such as a magnetic sensor and an arm to detect the position of the ultrasound probe but performs a signal processing on a B-mode image. Furthermore, the position of the ultrasound probe is determined using one B-mode image. Thus, the structure described above is free from the accumulation of error of PTL 1, and the constraint of movement at a constant speed of PTL 2.

In the above description, the reflective member image is detected after producing a B-mode image. However, note that the reflective member image may be detected from the signal before the signal is converted into the B-mode image. For example, the position where an amplitude value of echo is greater than the predetermined value may be detected as the reflective member image. The position of the reflective member image can be detected in a finer resolution by detecting the reflective member image from the signal before the B-mode image is produced.

In the above description, the signal having the highest derivative value of brightness with respect to a variation in the vertical direction in the pad area is detected as the reflective member image. However, a threshold value may be used so that a portion having a derivative value of brightness with respect to a variation in the vertical direction is greater than or equal to the threshold value for the first time is detected as the reflective member image. The threshold value is set such that the reflective member can be distinguished from the pad. For example, the threshold value may be a half value and the like of a range (dynamic range) of a derivative value of brightness in the pad area.

Further, for the detection, determination may be made based on brightness value instead of a derivative value of brightness. For example, the portion having the greatest brightness value in the pad area is detected as the reflective member image. Furthermore, when a threshold value is used, the signal having the brightness value that is greater than or equal to the threshold value for the first time may be detected as the reflective member image, in the same manner as with the detection based on the derivative value of brightness. The threshold value is set such that the reflective member image can be distinguished from the pad. For example, the threshold value may be a half value and the like of a range (dynamic range) of a brightness value in the pad area.

Furthermore, in the above description, the position of the detected reflective member image is directly converted into the position of the ultrasound probe. However, the position of the reflective member image may be recorded every time detection is performed. Then, the recorded values may be smoothed to obtain the position of the ultrasound probe. With the smoothing, a fluctuation due to a noise, an unsteady movement of a hand, and the like can be suppressed. Examples of the method of smoothing includes, but not limited to, a use of a median filter, and a mean filter. Furthermore, the smoothing may be performed after the conversion into the ultrasound probe position.

Furthermore, in the above description, the position of the ultrasound probe is calculated based on the look-up table 1401. However, a variation in the position at which the reflective member image is detected that is obtained every time the B-mode image is obtained may be used. For example, when it is assumed that (i) positions of the reflective member images in the vertical direction position in the three B-mode images X, Y, and Z are x, y, and z, respectively, (ii) the position of the ultrasound probe at the point of time when the image X is obtained is 0, and (iii) a scaling value is "s", the position of the ultrasound probe at the point of time when the image Y was obtained is calculated using Expression 1.

[Mathematical expression 1]

$$s \times (y-x) \qquad \text{(Expression 1)}$$

The position of the ultrasound probe at the point of time when the image Z was obtained is calculated using Expression 2.

[Mathematical expression 2]

$$s \times (z-x) \qquad \text{(Expression 2)}$$

Note that, if correspondence between the amount of movement of the ultrasound probe and the variation in the position of the reflective member image is known beforehand, the scaling value "s" can be calculated, and the variation in the position of the reflective member image can be converted into an absolute amount of movement of the ultrasound probe. The three-dimensional image producing unit 1007 arranges the B-mode images based on the amount of movement of the ultrasound probe to produce the three-dimensional image.

Note that, even when the position of the reflective member image in the vertical direction is not associated with the position of the ultrasound probe and the amount of movement of the ultrasound probe, it is possible to arrange the B-mode images appropriately. For example, it is assumed that a plurality of B-mode images such as a B-mode image 1, a B-mode image 2, . . . and a B-mode image N are produced and the position of the reflective member image in the vertical direction of the respective images is a position 1, a position 2, . . . and a position N. Here, positional information of each B-mode image, that is, the position 1, the position 2, . . . and the position N, is associated with the B-mode image 1, the B-mode image 2 . . . , and the B-mode image N, respectively. Then, the three-dimensional image is produced by arranging the B-mode images such that a ratio between "z" and "y" is always constant, where the "z" represents a difference in distance between the predetermined B-mode image i (i≤N) and the B-mode image 1, and the "y" represents a difference between the position i (i≤N), which is the position of the reflective member image in the vertical direction in the predetermined B-mode image, and the position 1.

As described in Embodiment 1 and as shown in FIG. 1 and the like, the reflective member 141 disposed inside the pad is in a substantially linear shape, and the distance between the main surface 15 and the reflective member 141 gradually varies according to the position in the main surface 15 of the pad. Thus, by arranging the B-mode images such that displacement of position of the reflective member 141 image in the vertical direction from a given reference point and displacement of position of the ultrasound probe from a given reference point are constant, it is possible to display continuity of the images more precisely. To achieve this, however, magnification of expansion and contraction on images in the z-direction of three-dimensional images is additionally used.

Note that, as described in Embodiment 1, the reflective member 141 does not necessarily have to be a continuous, single member but may be formed of a plurality of divided members. In other words, the shape of the reflective member in the cross-section in the yz-plane of the pad in FIG. 2 looks like a dotted line that is formed of a plurality of members. When the reflective member is formed of the divided members, not all the obtained B-mode images include the reflective member image. In this case, the arrangement of the B-mode images having the reflective member images may be determined, and where to arrange the B-mode images having no reflective member images may be determined, considering the similarity with the images having the reflective member images. Furthermore, the B-mode images having the reflective member images may be arranged, and the B-mode images having no reflective member images may be arranged in the order the tomographic image producing unit 1002 produced the images.

Embodiment 3

This embodiment describes another aspect of the pad, and another aspect of the ultrasound diagnostic apparatus.

First, an issue addressed in this embodiment is described with reference to FIG. 17.

Figure 17:
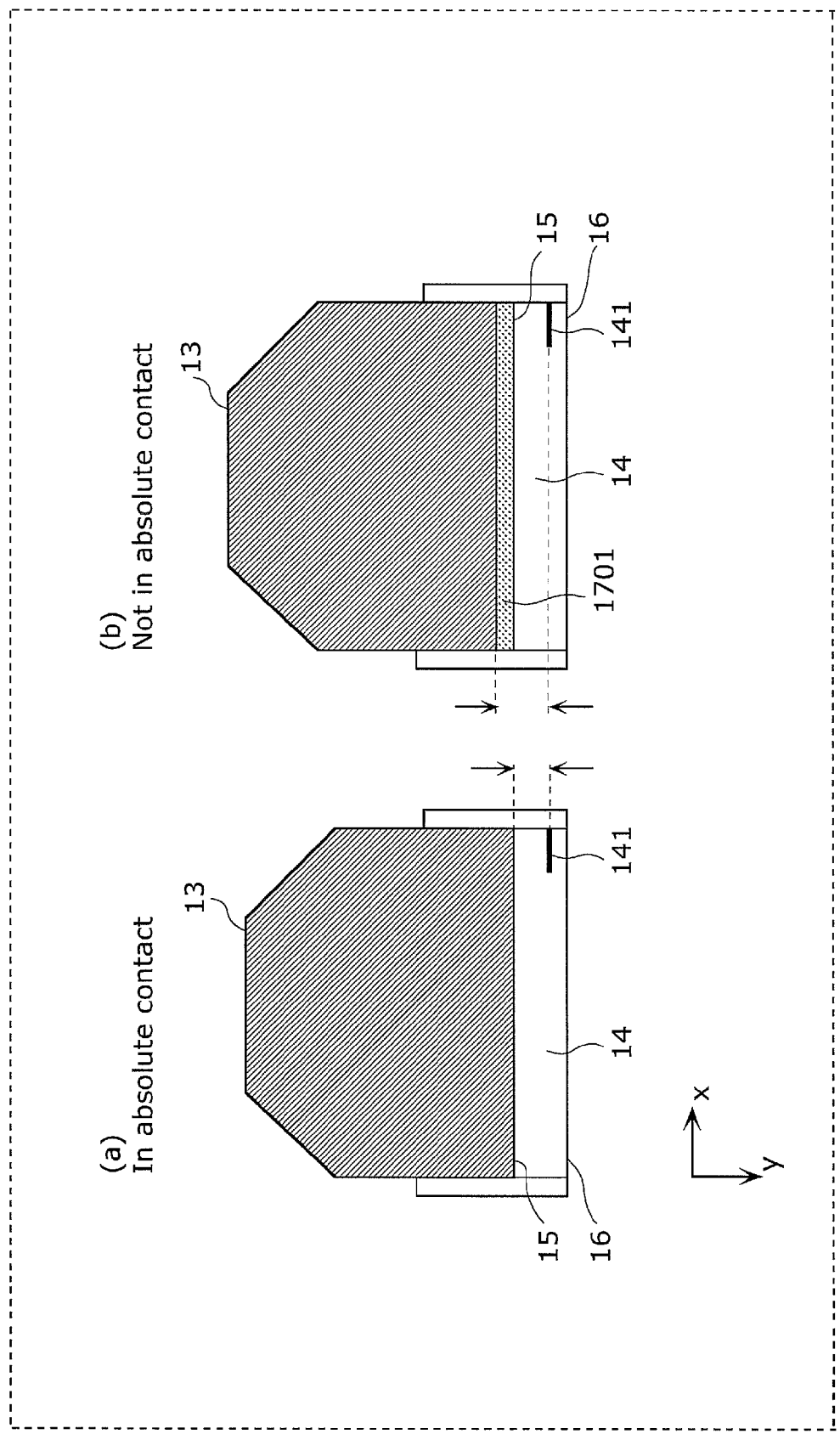

Shown in (a) in FIG. 17 is a cross-sectional view of the pad 14 when the ultrasound probe 13 is in absolute contact with the main surface 15 of the pad 14. Shown in (b) in FIG. 17 is a cross-sectional view of the pad 14 when a gap 1701 is present between the ultrasound probe 13 and the main surface 15 of the pad 14, and thus the ultrasound probe is not in absolute contact with the main surface 15 of the pad.

In Embodiments 1 and 2, it is described that the position of the ultrasound probe is calculated based on the vertical direction distance between the main surface of the pad and the reflective member. However, there may be a case where the ultrasound probe is disengaged from the main surface of the pad due to unsteady movement of a hand and the like. Then, the precise position of the ultrasound probe cannot be calculated because the distance between the surface of the ultrasound probe and the reflective member is greater than the distance between the main surface 15 and the reflective member. In view of the above, this embodiment describes a structure with which the precise position of the ultrasound probe can be calculated even when the ultrasound probe is disengaged from the main surface of the pad.

Figure 19:
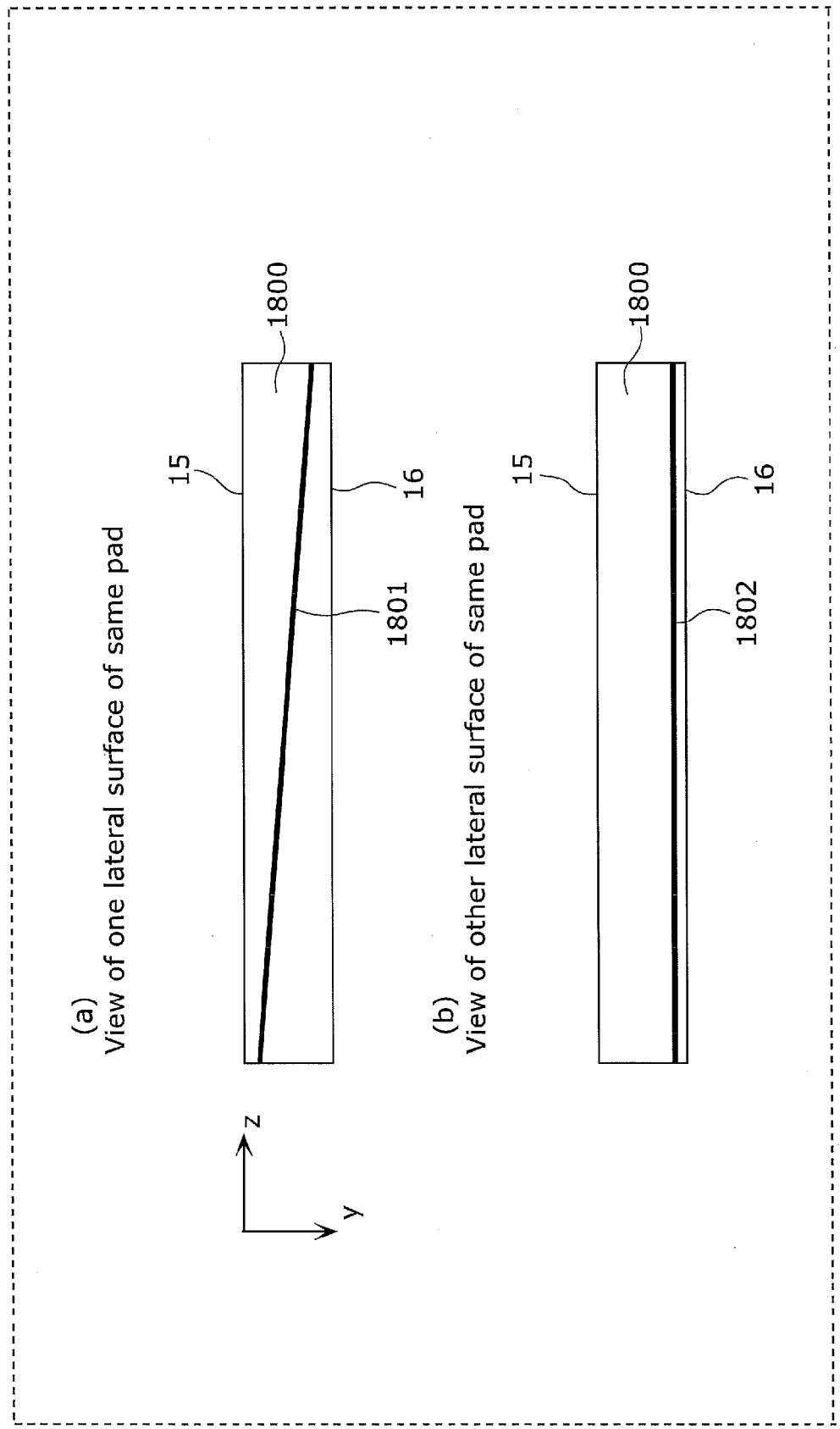

The following describes an ultrasound diagnostic adapter 3 according to this embodiment with reference to a perspective view in FIG. 18 and a lateral view in FIG. 19.

A pad 1800 according to this embodiment includes a reflective member 1801 and a reflective member 1802, which are linear-shaped reflective members arranged along both sides of the pad. In this case, as shown in FIG. 19, an at least one pair of the reflective members is arranged such that each of the reflective members has a different angle of inclination with respect to the main surface 15 of the pad 1800. In other words, depending on the position in the z-direction on the pad, the difference between (i) the distance between the main surface and the reflective member 1801 and (ii) the distance between the main surface and the reflective member 1802 varies.

The following describes a three-dimensional image displaying mechanism that produces a three-dimensional image based on signals obtained by moving the ultrasound probe on the pad.

The structure of the three-dimensional image displaying mechanism is the same as that according to Embodiment 2 and FIG. 10. Thus, the descriptions thereof are omitted.

FIG. 20 shows B-mode images produced by the tomographic image producing unit 1002 using the pad according to Embodiment 3. In the B-mode images, images of the reflective member 1801 and the reflective member 1802 are shown as high brightness areas, that is, 2002 and 2004, respectively. The vertical direction distance between two reflective member images is counted, for example, in a unit of the number of pixels 2005.

Next, the reflective member detection unit 1003 detects, from the B-mode image, the reflective member images 2002 and 2004 corresponding to the reflective member 1801 and the reflective member 1802, respectively. Note that, the specific method of detecting the reflective member is the same as that according to Embodiment 2. Thus, the descriptions thereof are omitted. The reflective member detection unit 1003 transmits, to the probe position calculation unit 1005, the position of the reflective member image in the vertical direction.

The probe position calculation unit 1005 calculates the position of the ultrasound probe based on the position of the reflective member image in the vertical direction in the B-mode image received from the reflective member detection unit 1003. Here, the reflective member detection unit 1003 is characterized by calculating the position of the ultrasound probe based on the vertical direction distance between the two reflective member images, instead of calculating the position of the ultrasound probe based on the position of one reflective member in the vertical direction. The probe position calculation unit 1005 includes a look-up table in which the position of the ultrasound probe is associated in one-to-one correspondence with the vertical direction distance between the reflective member images 2002 and 2004. The probe position calculation unit 1005 calculates the position of the ultrasound probe based on the look-up table and the vertical direction distance between the two reflective member images. An example of the look-up table is the same as that shown in FIG. 14, except that the table includes vertical direction distance between the reflective member images instead of the number of pixels.

Note that, in the same manner as Embodiment 2, the look-up table is reconfigurable. Specifically, the ultrasound probe is disposed at a predetermined position, and the position of the ultrasound probe and the vertical direction distance between the two reflective members are associated. For example, in the same manner as in FIG. 16 (here, however, note that the horizontal axis in FIG. 16 represents the vertical direction distance between the two reflective members), the number of pixels "a" between the two reflective member images detected when the ultrasound probe is placed at a position A, and the number of pixels "b" between the two reflective member images detected when the ultrasound probe is placed at a position B are used to obtain a line that passes the point (a, A) and the point (b, B). The look-up table is re-generated based on the line equation. It is apparent that the position of the ultrasound probe may be directly calculated using the line equation.

As described, the probe position calculation unit 1005 calculates the positional information of the ultrasound probe at the point of time when the predetermined B-mode image was obtained, and transmits the positional information to the tomographic image memory unit 1006. Here, whether to store in the tomographic image memory unit 1006 the B-mode image and the positional information of the ultrasound probe in association with each other or to store the B-mode image and the positional information of the ultrasound probe in time sequence may be determined arbitrarily.

Figure 21:
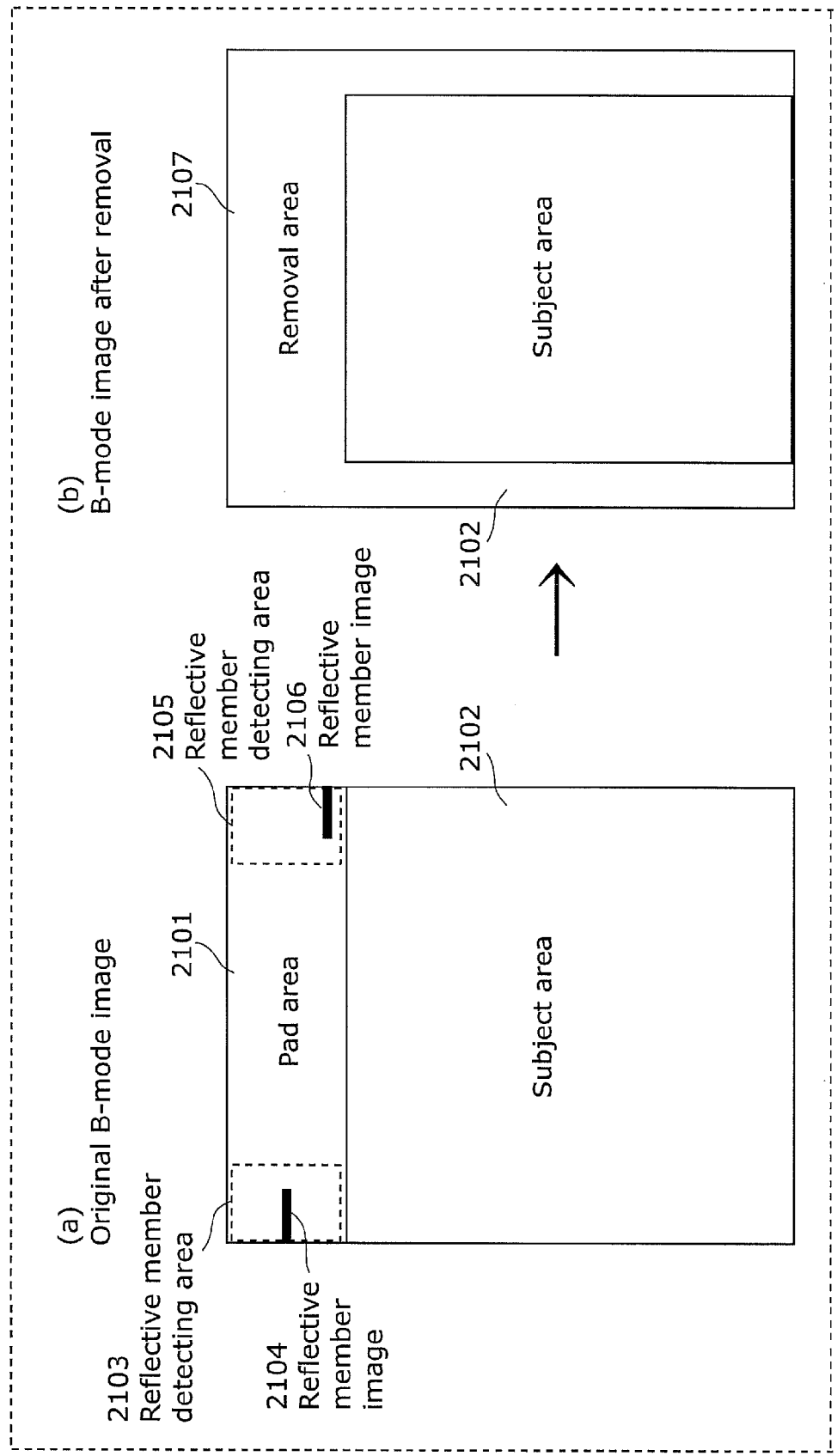

Next, as shown in FIG. 21, the unnecessary area removing unit 1004 removes a removal area (2107), which is the pad area and the area in which the reflective member is present in the B-mode image, and thus extracts from the B-mode image a subject area to be used for making a diagnosis.

The three-dimensional image producing unit arranges the B-mode images based on the positional information of the ultrasound probe, which is stored in the tomographic image memory unit 1006, to produce the three-dimensional image.

Note that the methods described in Embodiment 1 can be used to detect the reflective member image in the B-mode image, and to calculate the position of the ultrasound probe based on the reflective member image. However, in calculating the position of the ultrasound probe, note that the distance between a first reflective member and a second reflective member in the y-direction is used in this embodiment, while the distance between the main surface and the reflective member is used in Embodiment 1. For example, a scaling value "s" (i.e. absolute amount of movement of the ultrasound probe) may be calculated using the variation in the vertical direction distance between the pair of reflective members obtained every time the B-mode image is obtained.

Furthermore, the ultrasound diagnostic apparatus may include the probe position calculation unit 1005, and directly arrange the B-mode images based on the vertical direction distance between the first reflective member image and the second reflective member image obtained by the reflective member detection unit 1003. For example, it is assumed that a plurality of B-mode images such as a B-mode image 1, a B-mode image 2, . . . and a B-mode image N are produced, and the vertical distance between the first reflective member image and the second reflective member image shown in the respective images is position 1, position 2, . . . and position N. Here, positional information of each B-mode image, that is, a position 1, a position 2, . . . and a position N, is associated with the B-mode image 1, the B-mode image 2 . . . , and the B-mode image N, respectively. Then, the three-dimensional image is produced by arranging the B-mode images such that a ratio between "z" and "y" is always constant, where "z" represents a difference in distance between the predetermined B-mode image i (i≤N) and the B-mode image 1, and "y" represents a difference between the distance i (i≤N) in a B-mode image "i" and the distance 1 in the B-mode image 1. With the above-described method of producing the three-dimensional image, continuity of the images can be displayed more precisely. To achieve this, however, magnification of expansion and contraction of images in the z-direction in three-dimensional images is additionally used.

Note that, an example in FIG. 18 shows a structure in which the first reflective member 1801 is non-parallel to the main surface 15, and the second reflective member 1802 is parallel to the main surface 15. However, both the reflective members 1801 and 1802 may be non-parallel to the main surface 15. Furthermore, although the structure which includes a pair of reflective members (1801 and 1802) is described with reference to FIG. 18, it is apparent that the pad may include two or more pairs of the reflective members.

Figure 22:
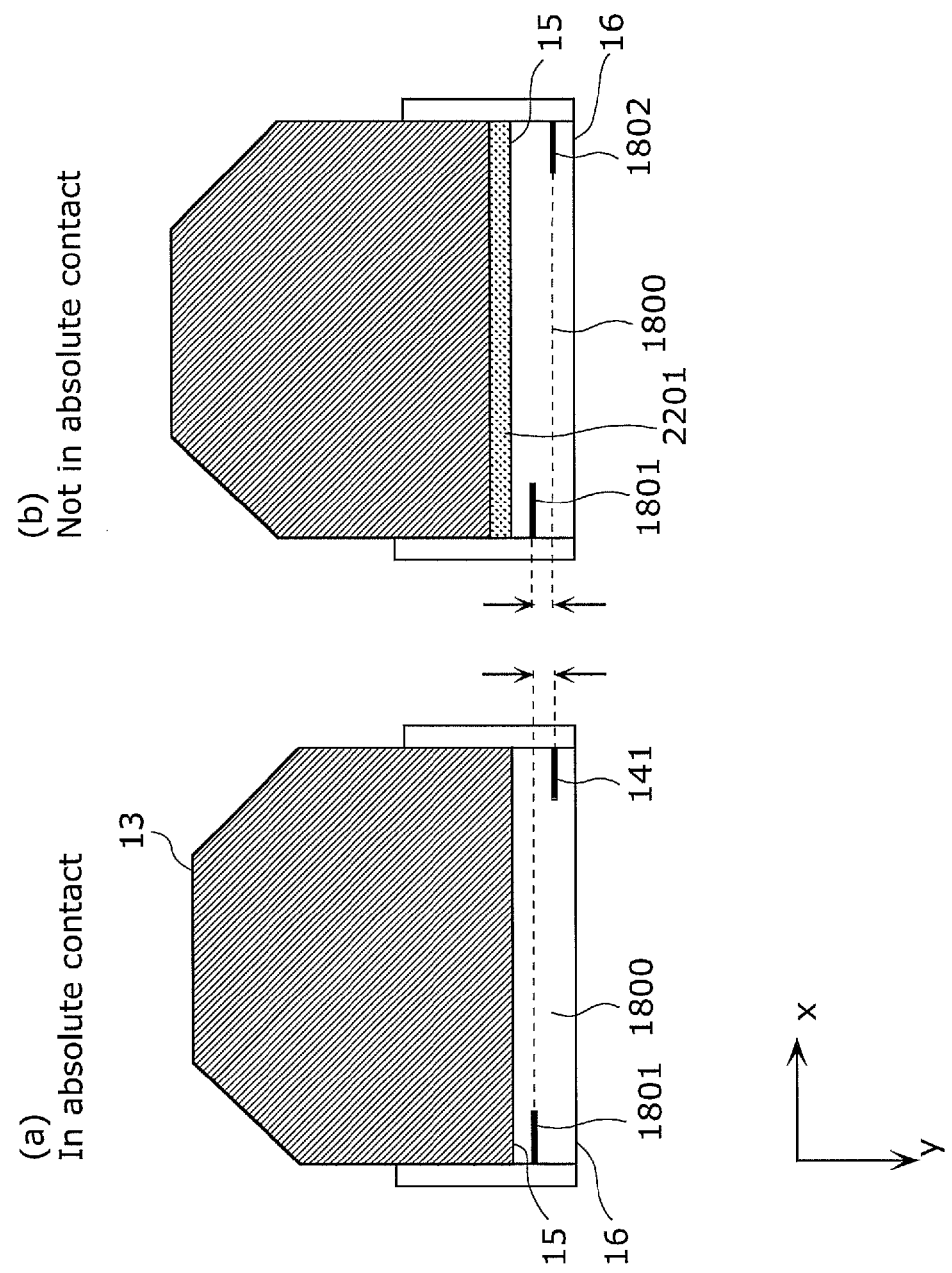

With the above-described pad, the position of the ultrasound probe can be calculated based on the distance between the two reflective members in the y-direction even when the ultrasound probe is not in absolute contact with the pad as shown in FIG. 22. Thus, it is possible to reduce influence due to the unsteady movement of a hand, and the like.

The following describes a variation of Embodiment 3.

Figure 23:
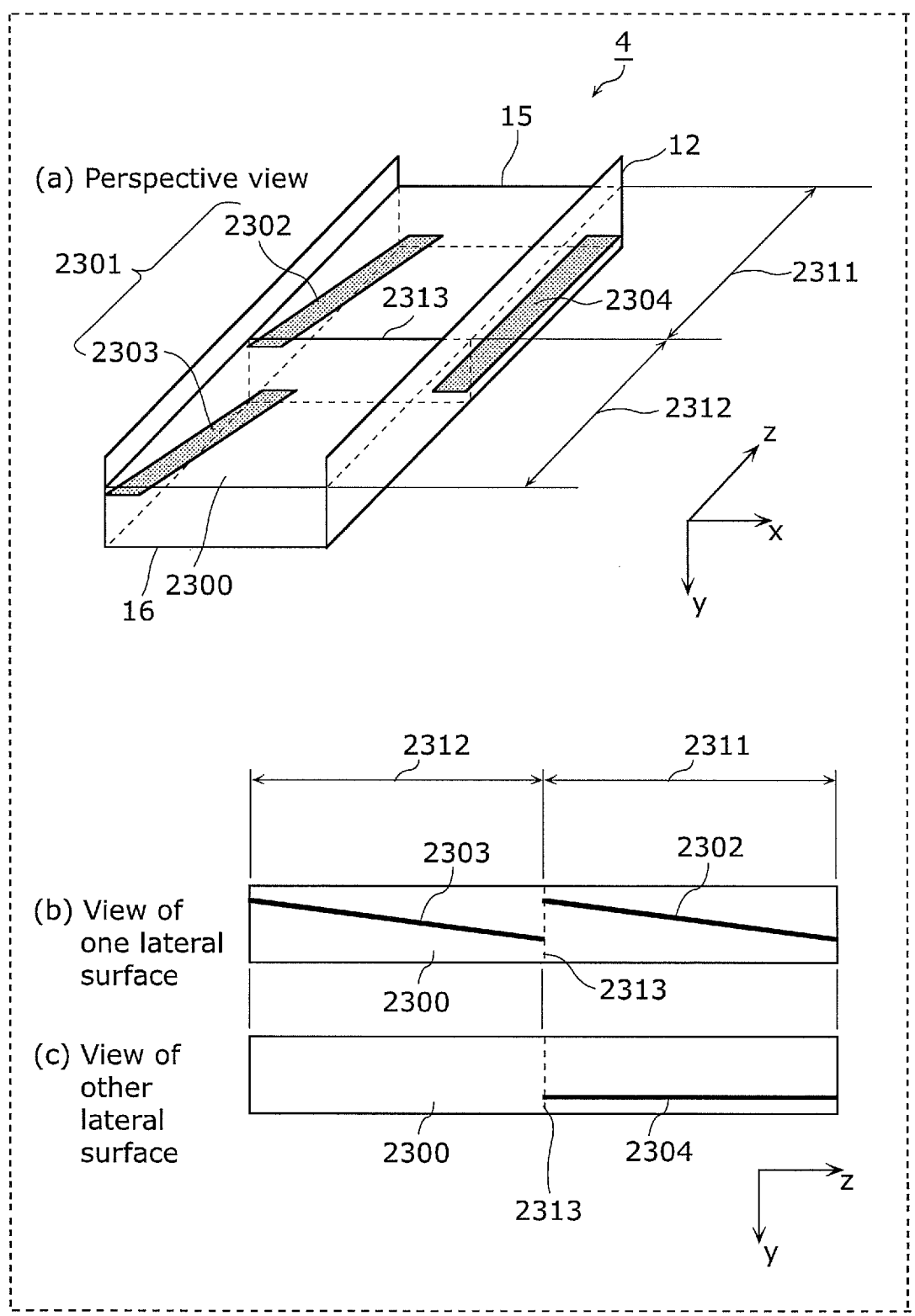

FIG. 23 shows an ultrasound diagnostic adapter 4 according to the variation of Embodiment 3. Shown in (*a*), (*b*), and (*c*) in FIG. 23 are a perspective view, a view of the lateral surface on the side near the first reflective member, and a view of the lateral surface on the side near the second reflective member, respectively. In the variation of this embodiment, a pad 2300, a first reflective member 2301, and the second reflective member 2304 are divided by a cross-section 2313 that is perpendicular to an extending direction (z-direction) of the reflective member. As shown in FIG. 23, each section is called a first pad area (2311) and a second pad area (2312). The first reflective member includes a portion 2302 disposed inside the first pad area (2311), and a portion 2303 disposed inside the second pad area. These portions 2302 and 2303 of the reflective member are arranged such that positional relationships of the portions of the first reflective member relative to the main surface match one another. Furthermore, the second reflective member is disposed parallel to the extending direction of the first reflective member as seen from the main surface side, and is disposed inside the first pad area (2311).

When this structure is scanned with ultrasound probe and the ultrasound probe is placed on the first pad area (2311), an image of the first reflective member portion 2302 and an image of the second reflective member 2304 are shown in the B-mode image. As the image of the second reflective member 2304 is detected, it is detected that the ultrasound probe is placed on the first area, and the position in the first area (2311) is detected based on the distance between the main surface and the portion 2302. Furthermore, when the ultrasound probe is placed on the second area, an image of the portion 2303 is shown in the B-mode image. The image of the second reflective member is not detected, which indicates that the ultrasound probe is placed on the second area, and the position in the second area (2312) is detected based on the distance between the main surface and the portion 2303. With this method, the position of the ultrasound probe can be detected. With this structure, even when the first reflective member has the same angle of inclination with respect to the main surface as the first reflective member according to Embodiment 1, the thickness of the pad can be reduced to ½ of the pad according to Embodiment 1. Thus, the subject area in the B-mode image can be increased.

Note that, although the above example described the case where the pad is divided into two areas, it is apparent that the pad can be divided into three or more areas. With such structure, the thickness of the pad can be reduced to 1/(the number of areas). Thus, the subject area in the B-mode image can be further increased.

Embodiment 4

This embodiment is characterized in that the position of the ultrasound probe can be calculated, even when a large area is to be displayed by using a plurality of pads.

FIG. 24 shows an example of an ultrasound diagnostic adapter according to this embodiment. An ultrasound diagnostic adapter 5 according to this embodiment can (i) identify on which pads the ultrasound probe is placed or (ii) rearrange, as necessary, the obtained B-mode images in the direction perpendicular to the scan direction of the ultrasound probe.

As shown in FIG. 24, the ultrasound diagnostic adapter 5 includes at least two pads (a pad 2400 and a pad 2410). Furthermore, each of the pads includes at least one pair of the reflective members. In other words, the ultrasound diagnostic adapter 5 includes at least four reflective members.

Figure 25:
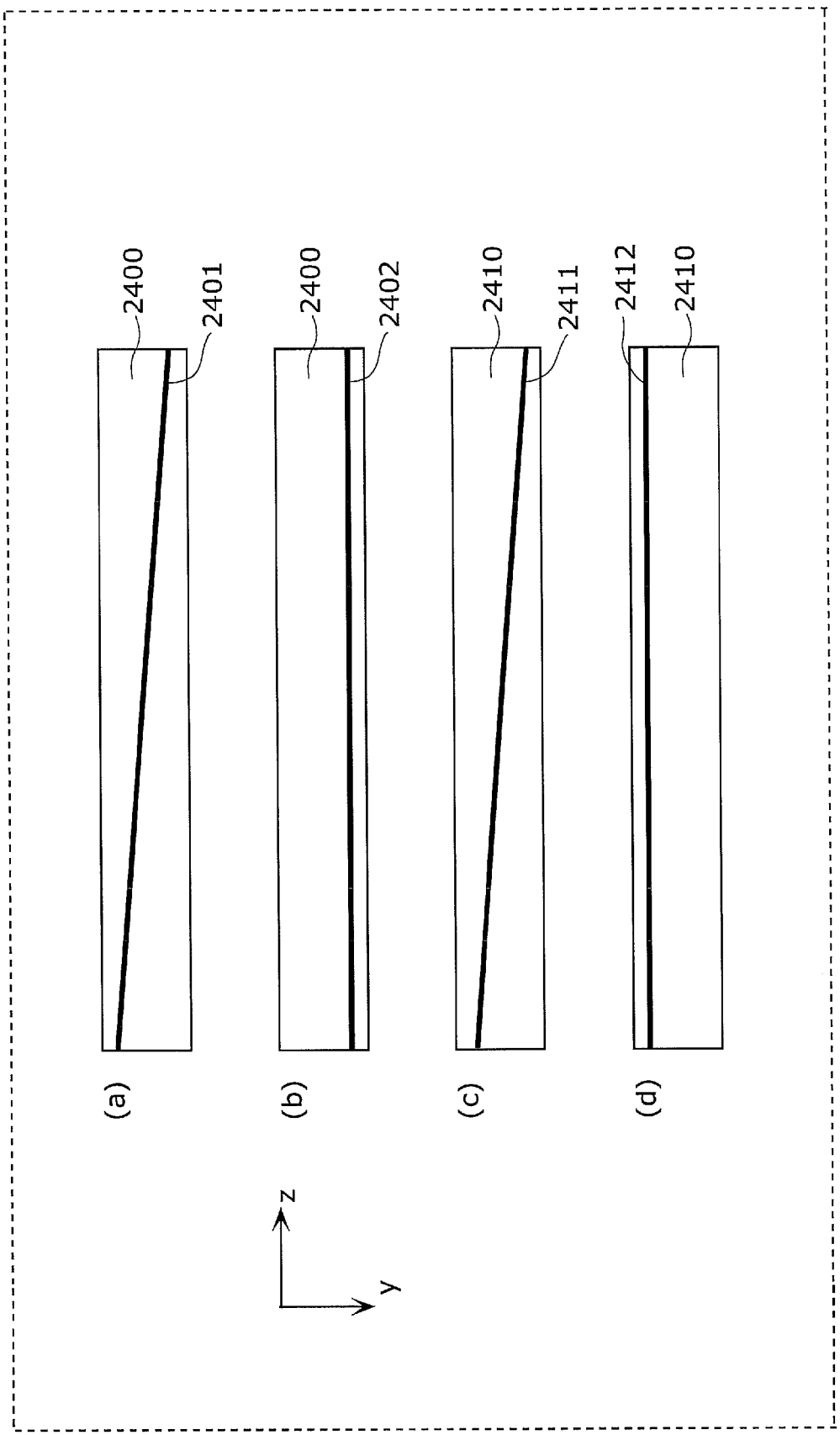

The ultrasound diagnostic adapter 5 shown in FIG. 24 includes (i) a reflective member 2401 and a reflective member 2402 that are disposed in the first pad 2400, and (ii) a reflective member 2411 and a reflective member 2412 that are disposed in the second pad 2410. Each of the reflective member 2401 and the reflective member 2411 is the reflective member (the first reflective member) that is disposed such that the distance between the main surface 15 and the reflective member varies in the extending direction. On the other hand, each of the reflective member 2402 and the reflective member 2412 is the reflective member (the second reflective member) that is arranged such that the distance between the main surface 15 and the reflective member in the extending direction of the reflective members is constant, and the reflective member 2402 and the reflective member 2412 are arranged such that distances between (i) the reflective member 2402 and the reflective member 2412 and (ii) the main surface in the extending direction are different from each another. Thus, the distance between the main surface 15 and the second reflective member, which is disposed parallel to the main surface 15, is different depending on whether the ultrasound probe is placed on the first pad 2400 or the ultrasound probe is placed on the second pad 2410. FIG. 25 shows a lateral view of each of the pads. Using the first reflective members 2401 and 2411, whether the ultrasound probe is disposed on the pad 2400 or on the pad 2410 is identified, by comparing the distance between (i) the main surface and (ii) the first reflective members 2401 and 2411. The position of the ultrasound probe on the pad can be identified based on the distance between (i) the main surface 15 and (ii) the second reflective members 2402 and 2412.

With the ultrasound diagnostic adapter 5, the ultrasound diagnostic apparatus determines on which pad the ultrasound probe is placed, that is, the position of the ultrasound probe in the x-direction. For example, the reflective member detection unit 1003 detects the images of the reflective member 2401 and the reflective member 2411 in the B-mode image, and detects the position of each of the reflective member images in the vertical direction. The probe position calculation unit 1005 includes a look-up table which indicates relationship between the position of the ultrasound probe in the x-direction and the position of the reflective member image in the vertical direction, and can identify on which pad the ultrasound probe is placed, based on the look-up table and the position of the reflective member image in the vertical direction. With this structure, it is possible to identify on which pad the ultrasound probe was disposed when each of the B-mode images was obtained.

Furthermore, for example, the distance between the main surface and the first reflective member may monotonically decrease or increase as the position of the pad progresses in the x-direction. Use of such a pad makes it possible to rearrange, as necessary, the obtained B-mode images in the x-direction without using the look-up table.

As described above, the pad can be identified by the second reflective members 2402 and 2412, and the position of the ultrasound probe on the pad can be identified by the first reflective members 2401 and 2411. Thus, the position of the ultrasound probe can be calculated even in a wide area where two pads are used.

Note that it has been described that the position of the ultrasound probe is calculated based on the distance between the main surface and each of the reflective members. However, in the same manner as Embodiment 3, the position of the ultrasound probe may be calculated based on the distance between the reflective members disposed inside the same pad.

Furthermore, although the above described the case where two pads are used, the number of pads may be increased.

Note that, the first reflective members 2401 and 2411 are used to calculate the position of the ultrasound probe in the z-direction, and may be disposed at an angle with respect to the main surface of the pad.

The following describes Variation 1 of Embodiment 4. FIG. 26 shows an ultrasound diagnostic adapter 6 according to Variation 1 of Embodiment 4.

In the above, the reflective members are arranged along both sides of the scan area of each of the pads. However, as shown in FIG. 26, the reflective member may be disposed only along one side of the scan area in such a manner that distance between the main surface and the reflective member is different for each of the pads. The reflective members do not have to be arranged on both sides of the scan area.

Figure 27:
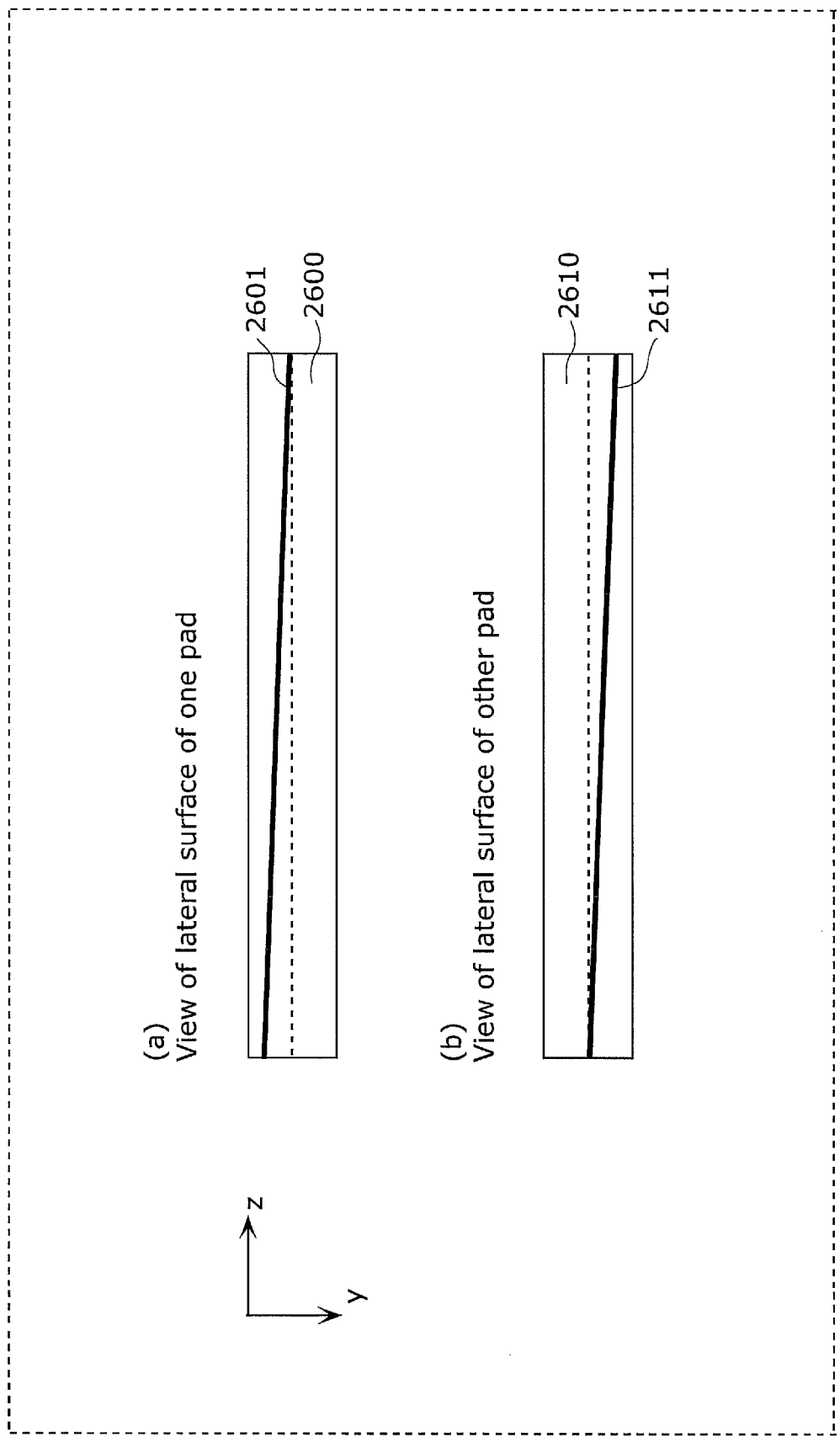

In Variation 1 of Embodiment 4, too, the ultrasound diagnostic adapter 6 includes two or more pads. In each pad, at least one reflective member (the first reflective member) is disposed at an angle with respect to the main surface 15. Here, the variation of Embodiment 4 is characterized in that the distance between the main surface and the reflective member is different for each pad. FIG. 27 shows views of lateral surfaces of pads included in Variation 1 of Embodiment 4. Shown in (a) and (b) in FIG. 27 are views of lateral surfaces of different pads. As shown in (a) and (b) in FIG. 27, the reflective members are disposed such that the distances between the main surface and the reflective members in the pad are different from each other. The ultrasound diagnostic apparatus includes, for example, a look-up table which indicates the relationship between the position of the reflective member on the edge of the pad and the position of the pad in the x-direction (i.e. the position of the ultrasound probe in the x-direction), and can add positional information of the ultrasound probe in the x-direction to the B-mode image.

Note that, for example, the position of the reflective member on the edge of the pad may monotonically decrease or increase as the position of the pad progresses in the x-direction. Use of such structure makes it possible to rearrange, as necessary, the obtained B-mode images in the x-direction without using the look-up table.

Note that FIG. 27 shows that first reflective members 2601 and 2611 are angled at the same angle with respect to the main surface. However, the angles of the first reflective members 2601 and 2611 may be different from each other.

The following describes Variation 2 of Embodiment 4.

According to Variation 2 of Embodiment 4, angles of the first reflective members arranged inside pads may be varied for each of the pads, and the value of the angle may be used to determine on which pads the ultrasound probe was placed when the B-mode image was obtained. For example the angle of each of the reflective member may be monotonically increased or monotonically decreased as the position of the pad increases in the x-direction. Then, the reflective member detection unit 1003 of the ultrasound diagnostic apparatus calculates the angle of the reflective member based on the position of the reflective member in the vertical direction in the series of B-mode images, add the angle information to each of the B-mode images, and store the B-mode images in the tomographic image memory unit 1006. The three-dimensional image producing unit 1007 arranges B-mode images in the z-direction to produce a three-dimensional image, and arrange the produced three-dimensional image in the x-direction based on the angle information.

The above-described structure makes it possible to more precisely arrange B-mode images to produce a three-dimensional image. Moreover, the three-dimensional images can be appropriately arranged in the direction (x-direction) perpendicular to the scan direction of the ultrasound probe.

The following describes Variation 3 of Embodiment 4.

According to Variation 3 of Embodiment 4, the ultrasound diagnostic adapter may include two or more pads. The relative position of the first reflective member to the pad as seen from the main surface side of the pad may vary for each of the pads.

Figure 28:
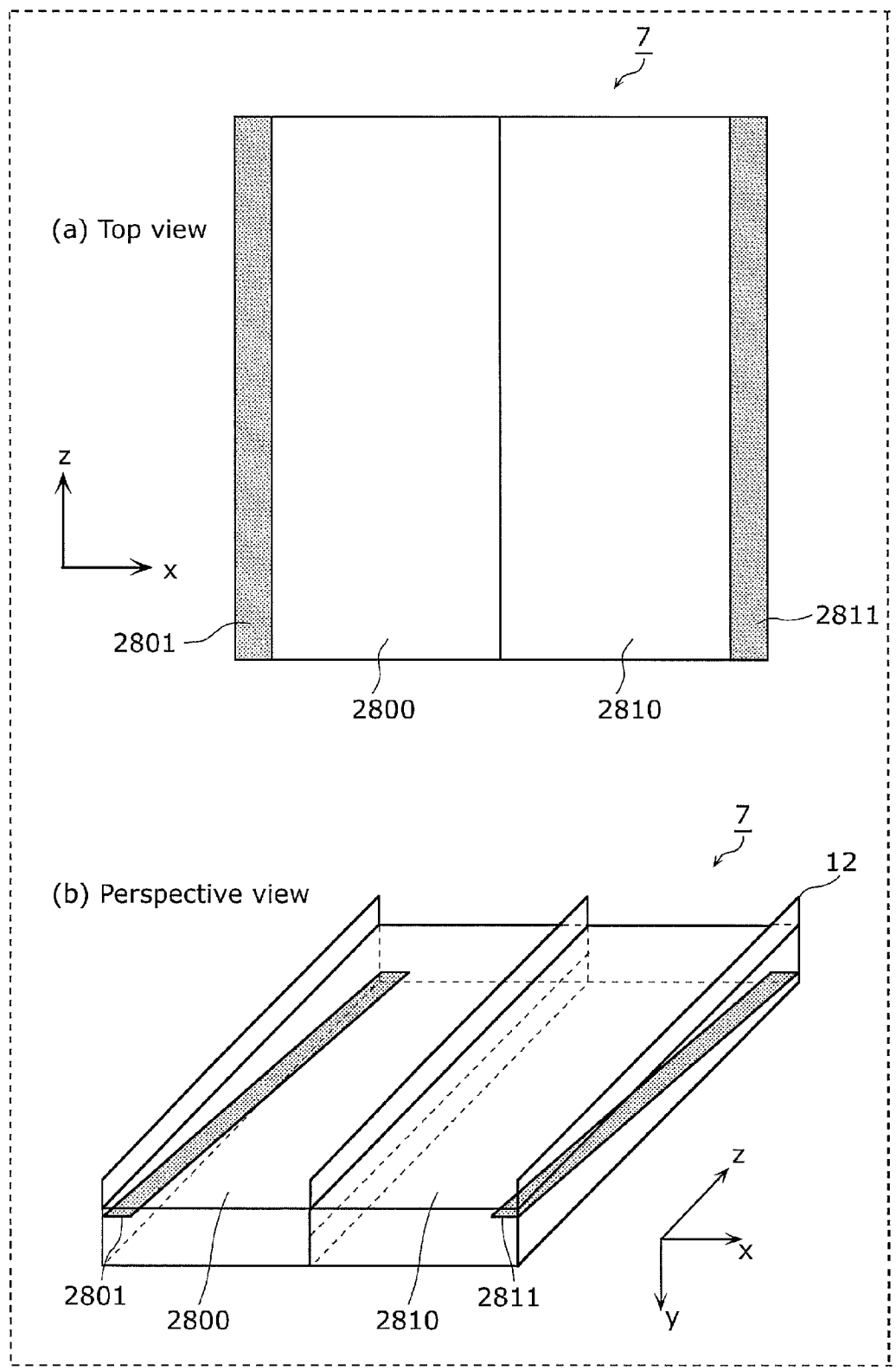

FIG. 28 shows an example of an ultrasound diagnostic adapter 7 according to Variation 3 of this embodiment. Shown in (a) and (b) in FIG. 28 are a top view and a perspective view, respectively. The (a) and (b) in FIG. 28 show: a pad 2800 in which a first reflective member 2801 is disposed; and a pad 2810 in which a first reflective member 2811 is disposed. In each of the pads, the first reflective member is disposed such that the relative position of the first reflective member to the pad as seen from the main surface side is different for each pad. In other words, in the top view (a) in FIG. 28, the reflective member 2801 is disposed on the left edge of the pad 2800, and the reflective member 2811 is disposed on the right edge of the pad 2810.

With this structure, the images of the reflective members 2801 and 2811 are detected in the different reflective member detecting area in the B-mode image. Thus, when the reflective member detecting area is different for each pad, the pad over which the ultrasound probe is scanning can be detected based on the area from which the reflective member image is detected. Further, the position of the ultrasound probe on the pad can be detected based on the distance between the main surface and the each of reflective members 2801 and 2811.

According to this structure, the area from which the reflective member is detected may be different for each pad. This makes it possible to detect the pad based on the relative position as seen from the main surface of the pad. In addition, the position of the ultrasound probe can be detected based on the distance between the main surface and each of the reflective members.

Embodiment 5

This embodiment describes another aspect of the pad, and another aspect of the ultrasound diagnostic apparatus.

Figure 29:
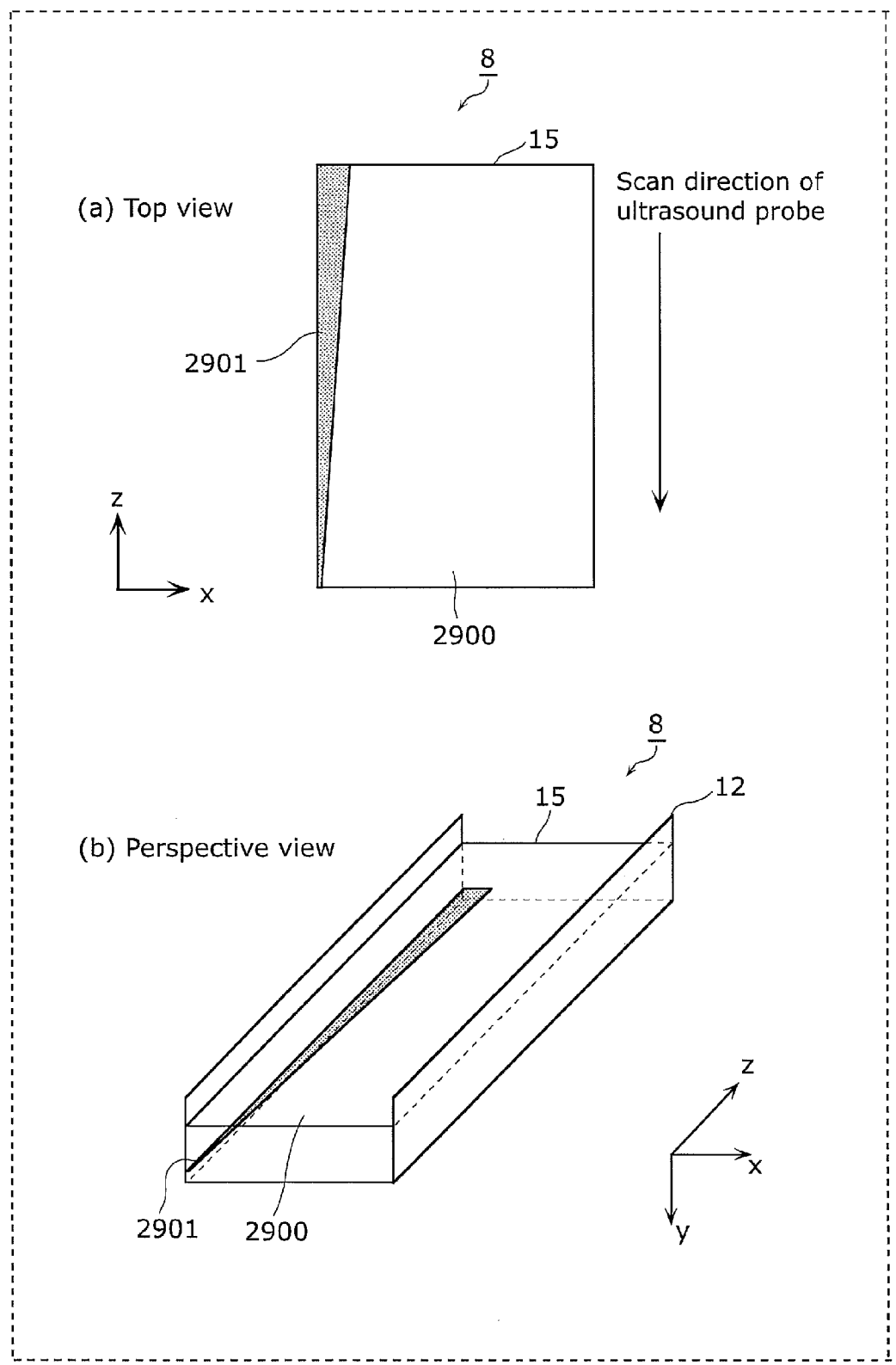

FIG. 29 shows a top view of an ultrasound diagnostic adapter 8 according to this embodiment. Piezoelectric elements (ultrasound transducers) are arranged in the ultrasound probe to form a single or a plurality of rows in the x-direction, and the ultrasound probe is moved in the z-direction. Although not illustrated, a scan assist mechanism such as a guide rail is disposed so that the ultrasound probe can be substantially linearly moved in the z-direction.

The ultrasound diagnostic adapter 8 includes: a pad 2900; and a reflective member 2901 disposed inside the pad 2900. The reflective member 2901 includes a material having a different acoustic impedance than the pad 2900. The reflective member 2901 is characterized in that the width as seen from the main surface 15 side is different depending on the position in the main surface 15. In other words, when viewed from the main surface 15 side, the width of the reflective member 2901 gradually varies along the predetermined direction. Specifically, in FIG. 29, the width of the reflective member gradually increases as progresses in the z-direction. Thus, the width of the reflective member 2901 in the x-direction varies as the ultrasound probe is moved. This makes it possible to more precisely calculate the position of the ultrasound probe based on the shape of the reflective member 2901.

Note that the position of the image of the reflective member 2901 in the vertical direction, that is, the distance between the main surface 15 and the image of the reflective member 2901 may be constant or different in the same manner as Embodiments 1 to 4.

The following describes a method for position detection using the reflective member 2901, and an ultrasound diagnostic apparatus which detects the position using the reflective member 2901.

The ultrasound diagnostic apparatus has a similar structure as the above-described FIG. 10. Thus, the descriptions thereof are omitted. Note that, in this embodiment, D1013 that is the output from the reflective member detection unit 1003 is different from Embodiment 1 to 4. The reflective member detection unit 1003 in this embodiment calculates and transmits to the probe position calculation unit the width of the reflective member image instead of the position of the reflective member image.

A method for calculating the position of the ultrasound probe using the reflective member 2901 is described with reference to FIG. 30. Step S3003 in FIG. 30 has different content than Step S1103 in FIG. 11. Other Steps that are S3001, S3002, S3004 and S3005 are the same as Step S1101, S1102, S1104 and S1105, respectively, in FIG. 11. Thus, detailed descriptions thereof are omitted.

In Steps S3001 and S3002, the ultrasound transmitting and receiving unit 1001 receives an echo, and the tomographic image producing unit 1002 generates a B-mode image. FIG. 31 shows a generated B-mode image. Here, the reflective member 2901 is formed such that the width of the reflective member 2901 varies gradually in the scan direction of the ultrasound probe. Thus, a width 3103 of the reflective member image displayed in the B-mode image varies depending on the position of the ultrasound probe.

In Step S3003, the width 3103 of the image of the reflective member 2901 is detected, for example, by the edge detection and the like. The ultrasound diagnostic apparatus has a look-up table in which a width of the reflective member image is associated in a one-to-one correspondence with a position of the ultrasound probe, and calculates using the table the position of the ultrasound probe based on the width of the reflective member image. Then, the ultrasound diagnostic apparatus appropriately arranges the images based on the position of the ultrasound probe to produce a three-dimensional image.

According to this embodiment, the reflective member does not have to be disposed at an angle inside the pad but may be disposed parallel to the main surface. This makes it possible to reduce the thickness of the pad. Consequently, an area in which a subject image is displayed can be increased in the B-mode image.

Note that descriptions on the common points as with Embodiments 2, 3, and 4 are omitted. Examples of the common points include: the look-up table is reconfigurable; Step S3004 for removing an unnecessary area from a B-mode image is optional; and a three-dimensional image may be directly produced such that the width 3103 of the reflective member image shown in each of the images monotonically increases or decreases, instead of producing a three-dimensional image by calculating the position of the ultrasound probe and then arranging the images.

Embodiment 6

This embodiment describes another aspect of a material included in the pad. In this embodiment, a portion between the reflective member and the main surface is made from a material having a sound velocity lower than a sound velocity of other portions of the pad. With this structure, the period of time from when the ultrasound probe transmits the ultrasound waves to when the ultrasound probe receives an echo can be increased. This makes it possible to reduce the thickness of the pad. Consequently, an area in which a subject image is displayed can be increased in the B-mode image.

Figure 32:
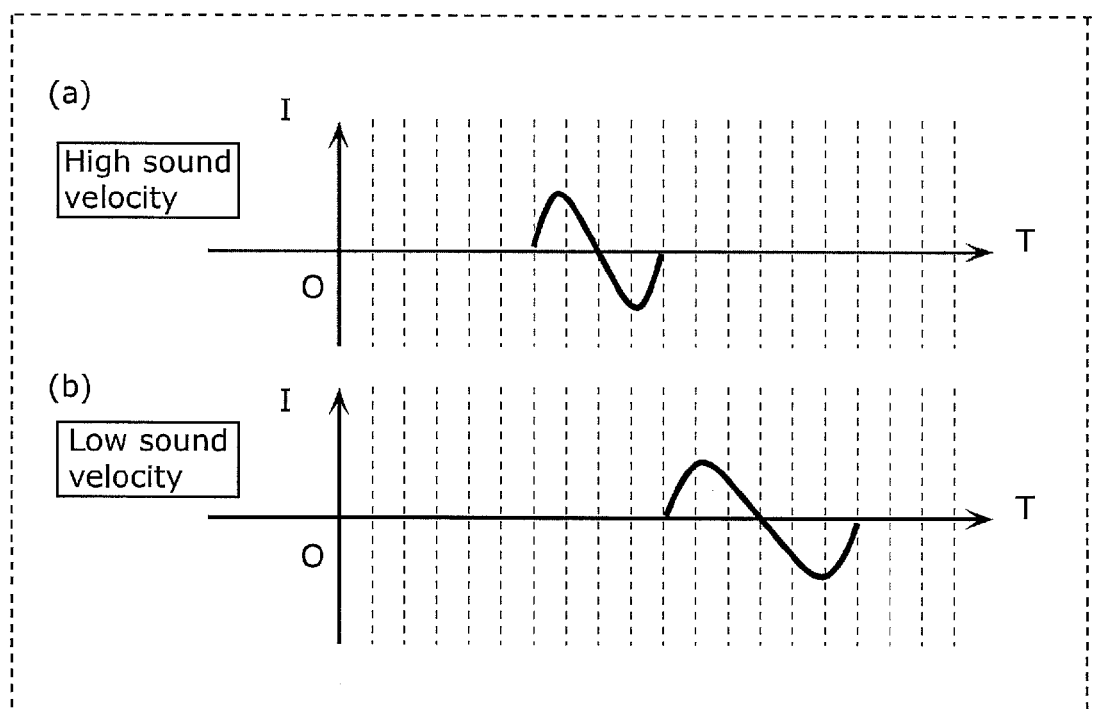

FIG. 32 shows, when it is assumed that the ultrasound probe transmits the ultrasound waves at time 0, the relationship between the time (horizontal axis) when the reflected waves (echo) is received and a sound intensity (vertical axis) of the echo at the time when the echo is received. Shown in (a) in FIG. 32 is the case where the portion between the reflective member and the main surface includes a material having an equivalent sound velocity (a material having a high sound velocity) as other portions. Shown in (b) in FIG. 32 is the case where the portion between the reflective member and the main surface includes a material having a lower sound velocity than other portions. The relationship shows that the time taken to receive the echo can be increased, when the portion between the reflective member and the main surface includes a material having a lower sound velocity than other portions.

The thickness of the pad can be reduced by disposing the reflective member at the position close to the main surface. However, when the reflective member is close to the main surface, the period of time from when the ultrasound probe transmits the ultrasound waves to when the ultrasound probe receives the echo is short. Sampling frequency of the ultrasound probe needs to be increased to receive the echo correctly, which is achieved by improving hardware performance and leads to an increase in cost. In view of this, a material having a lower sound velocity may be used for a substance included in the portion between the reflective member and the main surface. With this, the period of time from when the ultrasound probe transmits the ultrasound waves to when the ultrasound probe receives the echo can be increased.

FIG. 33 shows an ultrasound diagnostic adapter 9 according to this embodiment. Shown in (a), (b), and (c) in FIG. 33 are a perspective view, a lateral view, and a cross-sectional view of a surface perpendicular to the extending direction of the reflective member, respectively. A first reflective member 3301 is disposed inside a pad 3300. Furthermore, a substance of the portion between the first reflective member 3301 and the main surface 15 includes a material 3302 having a lower sound velocity than the material included in other portions of the pad. With this structure, the period of time from when the ultrasound probe transmits ultrasound waves to when the ultrasound probe receives the echo can be increased.

The above-described structure makes it possible to dispose the reflective member in a position close to the main surface without increasing the sampling frequency of the ultrasound probe, reduce the thickness of the pad, and, consequently increase the area in which a subject image is displayed in the B-mode image.

Note that the material between the reflective member and the back surface may includes (i) the same material as the reflective member, (ii) the same material as the substance included in other portions of the pad, (iii) or a material having a lower sound velocity than the substance included in the other portions of the pad.

Methods for implementing the exemplary embodiments of present disclosure have been described based on the embodiments. However, the implementation of the present disclosure is not limited to the above-described embodiments. Those skilled in the art will readily appreciate that various modifications may be made in these exemplary embodiments and other embodiments may be made by arbitrarily combining some of the structural elements of different exemplary embodiments without materially departing from the scope of the inventive concept.

It should be noted that a part or all of the structural elements constituting the respective apparatuses may be configured from a single system large scale integration (LSI). The system LSI is a super-mufti-function LSI manufactured by integrating structural units on one chip, and is specifically a computer system including a microprocessor, a read-only memory (ROM), a random-access memory (RAM), and the like. The RAM stores a computer program. The microprocessor operates according to the computer program so that the system LSI can perform its function.

Furthermore, each unit of structural elements included in the above-described apparatuses may be made as separate individual chips or as a single chip to include a part or all thereof.

The name used here is LSI, but it may also be called IC, system LSI, super LSI, or ultra LSI depending on the degree of integration. Moreover, ways to achieve integration are not limited to the LSI, and special circuit or general purpose processor and so forth can also achieve the integration. It is also acceptable to use an FPGA (Field Programmable Gate Array) that is programmable after the LSI has been manufactured, and a reconfigurable processor in which connections and settings of circuit cells within the LSI are reconfigurable.

In the future, if integrated circuit technology that replaces LSI appears through progress in semiconductor technology or other derived technology, that technology can naturally be used to carry out integration of structural elements. Application of biotechnology is one such possibility.

In the exemplary embodiments, each of the structural elements may be implemented as a piece of dedicated hardware or implemented by executing a software program appropriate for the structural elements. The structural elements may also be implemented by a program execution unit such as a CPU or a processor which reads and executes a software program recorded on a recording medium such as a hard disk or a semiconductor memory. Here, the ultrasound diagnostic apparatuses in the above-described embodiments are implemented by executing a software program below.

Specifically, the program causes a computer to execute detecting, from among signals received by the ultrasound probe, a signal of reflected waves from the first reflective member; and detecting, from the signal detected in the detecting of a signal, a position of the ultrasound probe based on at least one of (i) a distance between the first reflective member and the main surface and (ii) a width of the first reflective member as seen from the side of the main surface.

Although only some exemplary embodiments have been described in detail above, those skilled in the art will readily appreciate that various modifications may be made in these exemplary embodiments without materially departing from the principles and spirit of the inventive concept.

INDUSTRIAL APPLICABILITY

One or more exemplary embodiments of the present disclosure are applicable to an ultrasound diagnostic adapter and an ultrasound diagnostic apparatus, and can be used for the diagnosis of the presence of a lesion and comparison with another modality especially as an ultrasound diagnostic adapter and an ultrasound diagnostic apparatus that can display information of a large area inside the living body as a three-dimensional image. In particular, the ultrasound diagnostic adapter and the ultrasound diagnostic apparatus according to one or more exemplary embodiments of the present disclosure do not require a large apparatus but are compact, and thus very portable and useful for making a diagnosis visiting patients and the like.

The invention claimed is:

1. An ultrasound diagnostic adapter to be interposed between an ultrasound probe and a subject and used when diagnosing the subject using the ultrasound probe, the ultrasound probe transmitting and receiving ultrasound waves, said ultrasound diagnostic adapter comprising:
   a pad which has (i) a main surface that is a surface on a side where the ultrasound probe is to be disposed, and (ii) a back surface that is a surface which is opposite to the main surface and is on a side where the subject is to be disposed;
   a first reflective member which extends inside said pad and made from a material having an acoustic impedance different from an acoustic impedance of a material included in said pad; and
   a second reflective member which extends inside said pad along an extending direction of said first reflective member and is made from a material having an acoustic impedance different from the acoustic impedance of the material included in said pad,
   wherein:
   said pad has, on the main surface, a scan area with a width according to which the ultrasound probe is slidable with respect to the pad,
   said first reflective member and said second reflective member are arranged in the scan area of said pad so as to occupy only a partial area of the scan area,
   said first reflective member and said second reflective member are respectively disposed at first and second ends of said pad in a direction perpendicular to a depth direction as seen from the main surface,
   said first reflective member is disposed such that at least one of (i) a distance between said first reflective member and the main surface and (ii) a width of said first reflective member as seen from the side of the main surface varies in a direction in which the ultrasound probe is slidable, depending on a position on the main surface, and
   said first reflective member and said second reflective member are disposed such that an inclination angle of said first reflective member is different from an inclination angle of said second reflective member, the inclination angle of said first reflective member indicating a degree of variation in distance between said first reflective member and the main surface in the extending direction, and the inclination angle of said second reflective member indicating a degree of variation in distance between said second reflective member and the main surface in the extending direction.

2. The ultrasound diagnostic adapter according to claim 1, wherein:
   said first reflective member is divided into a plurality of portions by a cross-section perpendicular to the extending direction of said first reflective member,
   each of the portions of said first reflective member is disposed such that a distance between the portion of said first reflective member and the main surface varies in the extending direction,
   the portions of said first reflective member are arranged such that positional relationships of the portions of said first reflective member relative to the main surface match one another, and
   said second reflective member is disposed such that a distance between said second reflective member and the main surface does not vary in the extending direction.

3. The ultrasound diagnostic adapter according to claim 1, further comprising:
   a plurality of pad sets each of which includes said pad, said first reflective member, and said second reflective member,
   wherein each of said first reflective members included in said pad sets is disposed such that a distance between said first reflective member and the main surface varies in the extending direction,
   each of said second reflective members included in said pad sets is disposed such that a distance between said second reflective member and the main surface does not vary in the extending direction, and
   said second reflective members included in said pad sets are arranged such that respective distances between (i) said second reflective members and (ii) the main surface in the extending direction are different from one another.

4. The ultrasound diagnostic adapter according to claim 1, further comprising:
   a plurality of pad sets each of which includes said pad and said first reflective member,
   wherein said first reflective members included in said pad sets are arranged such that distances between (i) said first reflective members and (ii) the main surface are not equal to one another.

5. The ultrasound diagnostic adapter according to claim 1, further comprising:
   a plurality of pad sets each of which includes said pad and said first reflective member,
   wherein a relative position of said first reflective member to said pad as seen from the side of the main surface is different for each of said pad sets.

6. The ultrasound diagnostic adapter according to claim 1, further comprising:
   a first guide rail disposed along the extending direction of said first reflective member; and
   a slider which is configured to hold the ultrasound probe and is moveable along said first guide rail.

7. The ultrasound diagnostic adapter according to claim 1, further comprising:
   two guide rails arranged along the extending direction of said first reflective member and said second reflective member; and
   a slider which is held between said two guide rails, wherein said slider is configured to hold the ultrasound probe and is moveable along said two guide rails.

8. The ultrasound diagnostic adapter according to claim 7, wherein:
   said pad is disposed between said two guide rails as seen from the side of the main surface, and
   each of said two guide rails has a thickness greater than a thickness of said pad in a direction perpendicular to the main surface.

9. The ultrasound diagnostic adapter according to claim 1, wherein said first reflective member is disposed away from the back surface of said pad.

10. The ultrasound diagnostic adapter according to claim 1, wherein:
said pad includes (i) a first pad portion positioned on the side of the main surface and (ii) a second pad portion positioned on the side of the back surface, and
said first reflective member is disposed inside said first pad portion.

11. The ultrasound diagnostic adapter according to claim 10, wherein said second pad portion is made from a material having a modulus of elasticity lower than a modulus of elasticity of a material included in said first pad portion.

12. The ultrasound diagnostic adapter according to claim 1, wherein said pad is made from a material which has a sound velocity ranging from 1450 (m/s) to 1585 (m/s), and an average sound velocity of 1530 (m/s).

13. The ultrasound diagnostic adapter according to claim 1, wherein a portion of said pad which is disposed between said first reflective member and the main surface is made from a material having a sound velocity lower than a sound velocity of another portion inside said pad.

14. An ultrasound diagnostic apparatus comprising:
(A) an ultrasound diagnostic adapter to be interposed between an ultrasound probe and a subject and used when diagnosing the subject using the ultrasound probe, the ultrasound probe transmitting and receiving ultrasound waves,
wherein said ultrasound diagnostic adapter comprises:
a pad which has (i) a main surface that is a surface on a side where the ultrasound probe is to be disposed, and (ii) a back surface that is a surface which is opposite to the main surface and is on a side where the subject is to be disposed;
a first reflective member which extends inside said pad and made from a material having an acoustic impedance different from an acoustic impedance of a material included in said pad; and
a second reflective member which extends inside said pad along an extending direction of said first reflective member and is made from a material having an acoustic impedance different from the acoustic impedance of the material included in said pad,
wherein:
said pad has, on the main surface, a scan area with a width according to which the ultrasound probe is slidable with respect to the pad,
said first reflective member and said second reflective member are arranged in the scan area of said pad so as to occupy only a partial area of the scan area,
said first reflective member and said second reflective member are respectively disposed at first and second ends of said pad in a direction perpendicular to a depth direction as seen from the main surface,
said first reflective member is disposed such that at least one of (i) a distance between said first reflective member and the main surface and (ii) a width of said first reflective member as seen from the side of the main surface varies in a direction in which the ultrasound probe is slidable, depending on a position on the main surface, and
said first reflective member and said second reflective member are disposed such that an inclination angle of said first reflective member is different from an inclination angle of said second reflective member, the inclination angle of said first reflective member indicating a degree of variation in distance between said first reflective member and the main surface in the extending direction, and the inclination angle of said second reflective member indicating a degree of variation in distance between said second reflective member and the main surface in the extending direction;
(B) an ultrasound probe which transmits and receives ultrasound waves; and
(C) a processor or circuit which is configured to:
detect, from among signals received by said ultrasound probe, a signal of reflected waves from said first reflective member; and
detect, from the detected signal, a position of said ultrasound probe based on at least one of (i) a distance between said first reflective member and the main surface and (ii) a width of said first reflective member as seen from the side of the main surface.

15. The ultrasound diagnostic apparatus according to claim 14, wherein said processor or circuit is configured to detect a signal which is received from said pad and has an amplitude greater than or equal to a predetermined threshold from among the signals received by said ultrasound probe, as the signal from said first reflective member.

16. The ultrasound diagnostic apparatus according to claim 14, wherein said processor or circuit is configured to detect a signal which is received from said pad and has a greatest amplitude from among the signals received by said ultrasound probe, as the signal from said first reflective member.

17. The ultrasound diagnostic apparatus according to claim 14, wherein said processor or circuit is configured to detect a signal which is received from said pad and has a derivative value of an amplitude greater than or equal to a predetermined threshold from among the signals received by said ultrasound probe, as the signal from said first reflective member.

18. The ultrasound diagnostic apparatus according to claim 14, wherein said processor or circuit is configured to detect a signal which is received from said pad and has a greatest derivative value of an amplitude from among the signals received by said ultrasound probe, as the signal from said first reflective member.

19. The ultrasound diagnostic apparatus according to claim 14, wherein said processor or circuit is configured to calculate the position of said ultrasound probe, based on at least one of (i) a detected distance between said first reflective member and the main surface and (ii) a detected width of said first reflective member as seen from the side of the main surface, according to a relational expression that indicates at least one of relationships of the position of said ultrasound probe to (i) the detected distance between said first reflective member and the main surface and (ii) the detected width of said first reflective member as seen from the side of the main surface.

20. The ultrasound diagnostic apparatus according to claim 19, wherein said processor or circuit is configured to calibrate the relational expression using at least one of (i) the distance between said first reflective member and the main surface and (ii) the width of said first reflective member as seen from the side of the main surface that are detected between when said ultrasound probe is disposed at a first predetermined position and when said ultrasound probe is moved to a second predetermined position that is different from the first predetermined position.

21. The ultrasound diagnostic apparatus according to claim 14, wherein said processor or circuit is further configured to detect positions of said first reflective member obtained over a course of time and calculate an amount of movement between the positions of said ultrasound probe.

22. An ultrasound measurement method for measuring a subject by using an ultrasound diagnostic adapter and an ultrasound probe, wherein said ultrasound diagnostic adapter is configured to be interposed between the ultrasound probe and the subject and used when diagnosing the subject using the ultrasound probe, the ultrasound probe transmitting and receiving ultrasound waves, wherein said ultrasound diagnostic adapter comprises:
a pad which has (i) a main surface that is a surface on a side where the ultrasound probe is to be disposed, and (ii) a back surface that is a surface which is opposite to the main surface and is on a side where the subject is to be disposed;
a first reflective member which extends inside said pad and made from a material having an acoustic impedance different from an acoustic impedance of a material included in said pad; and
a second reflective member which extends inside said pad along an extending direction of said first reflective member and is made from a material having an acoustic impedance different from the acoustic impedance of the material included in said pad,
wherein:
said pad has, on the main surface, a scan area with a width according to which the ultrasound probe is slidable with respect to the pad,
said first reflective member and said second reflective member are arranged in the scan area of said pad so as to occupy only a partial area of the scan area,
said first reflective member and said second reflective member are respectively disposed at first and second ends of said pad in a direction perpendicular to a depth direction as seen from the main surface,
said first reflective member is disposed such that at least one of (i) a distance between said first reflective member and the main surface and (ii) a width of said first reflective member as seen from the side of the main surface varies in a direction in which the ultrasound probe is slidable, depending on a position on the main surface, and
said first reflective member and said second reflective member are disposed such that an inclination angle of said first reflective member is different from an inclination angle of said second reflective member, the inclination angle of said first reflective member indicating a degree of variation in distance between said first reflective member and the main surface in the extending direction, and the inclination angle of said second reflective member indicating a degree of variation in distance between said second reflective member and the main surface in the extending direction; and wherein said ultrasound measurement method comprises:
detecting, from among signals received by the ultrasound probe, a signal of reflected waves from the first reflective member; and
detecting, from the signal of the reflected waves from the first reflective member which is detected in said detecting of a signal, a position of the ultrasound probe based on at least one of (i) a distance between the first reflective member and the main surface and (ii) a width of the first reflective member as seen from the side of the main surface.

23. The ultrasound diagnostic adapter according to claim 1, wherein said first reflective member is disposed on an edge of the scan area so as to extend along an extending side of the scan area.

24. The ultrasound diagnostic adapter according to claim 1, wherein the scan area is a square area or a rectangular area in the main surface.

25. The ultrasound diagnostic adapter according claim 2, wherein:
said pad includes a first area and a second area in which the portions of said first reflective member divided by the cross-section are respectively disposed, and
said second reflective member is disposed in the first area, and is not disposed in the second area.

26. The ultrasound diagnostic apparatus according to claim 14, wherein said processor or circuit is configured to:
store data that indicates an association between a distance of said first reflective member and the main surface and a distance between said second reflective member and the main surface;
detect, from among signals received by said ultrasound probe, the signal of reflected waves from said first reflective member, and a signal of reflected waves from said second reflective member; and
calculate, from the detected signals of reflected waves from said first reflective member and said second reflective member, the position of said ultrasound probe based on said data, the distance between said first reflective member and the main surface, and the distance between said second reflective member and the main surface.

* * * * *